(12) United States Patent
Kim et al.

(10) Patent No.: US 11,020,007 B2
(45) Date of Patent: Jun. 1, 2021

(54) PHOTOACOUSTIC IMAGING DIAGNOSIS APPARATUS AND METHOD OF CONTROLLING THE SAME

(71) Applicant: SAMSUNG MEDISON CO., LTD., Hongcheon-gun (KR)

(72) Inventors: Beom-gyu Kim, Hongcheon-gun (KR); Jin-woo Jung, Hongcheon-gun (KR); Jae-ho Lee, Seoul (KR); Deok-woo Choi, Hongcheon-gun (KR); Won-jae Lee, Seoul (KR); Hyo-keun Lim, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 285 days.

(21) Appl. No.: 15/696,933

(22) Filed: Sep. 6, 2017

(65) Prior Publication Data

US 2018/0177406 A1 Jun. 28, 2018

(30) Foreign Application Priority Data

Dec. 26, 2016 (KR) .................. 10-2016-0179313

(51) Int. Cl.
*A61B 5/00* (2006.01)

(52) U.S. Cl.
CPC .......... *A61B 5/0095* (2013.01); *A61B 5/4244* (2013.01); *A61B 5/7282* (2013.01);
(Continued)

(58) Field of Classification Search
CPC ........................... A61B 5/0095; A61B 5/0093
See application file for complete search history.

(56) References Cited

U.S. PATENT DOCUMENTS

2003/0000535 A1* 1/2003 Galloway, Jr. .......... A61B 34/20
128/898
2011/0208061 A1* 8/2011 Chang .................. A61B 8/0833
600/458
(Continued)

FOREIGN PATENT DOCUMENTS

EP 2980753 A1 2/2016
EP 3100746 A1 12/2016
(Continued)

OTHER PUBLICATIONS

Valluru et al. "Photoacoustic Imaging in Oncology: Translational Preclinical and Early Clinical Experience". Radiology: vol. 280: No. 2—Aug. 2016. (Year: 2016).*

(Continued)

*Primary Examiner* — Serkan Akar
*Assistant Examiner* — Jillian K. McGough
(74) *Attorney, Agent, or Firm* — Sughrue Mion, PLLC

(57) ABSTRACT

A method of controlling a photoacoustic imaging diagnosis apparatus includes irradiating to an object an optical signal having a wavelength corresponding to an optical energy absorption wavelength of a contrast medium that is injected to the object; receiving a photoacoustic signal generated from the object in response to the optical signal; generating scan information representing an intensity of the photoacoustic signal based on the photoacoustic signal; determining a damage degree of the object by using a variation in the intensity of the photoacoustic signal during a preset time period included in the scan information; and displaying the damage degree of the object.

15 Claims, 22 Drawing Sheets

(52) U.S. Cl.
 CPC .............. *A61B 5/742* (2013.01); *A61B 5/743* (2013.01); *A61B 5/7475* (2013.01); *A61B 2576/00* (2013.01)

(56) References Cited

U.S. PATENT DOCUMENTS

| | | | | |
|---|---|---|---|---|
| 2014/0005556 A1* | 1/2014 | Hirota | .................. | A61B 5/0095 600/476 |
| 2015/0025373 A1 | 1/2015 | Kim et al. | | |
| 2016/0150990 A1 | 6/2016 | Ohkoba et al. | | |
| 2017/0333575 A1* | 11/2017 | Kondo | ............... | A61K 49/0034 |
| 2018/0280547 A1* | 10/2018 | Saji | .................... | A61K 49/0032 |

FOREIGN PATENT DOCUMENTS

| | | | | |
|---|---|---|---|---|
| EP | 3100746 B1 * | 1/2019 | ............. | A61K 49/22 |
| KR | 1020150010909 A | 1/2015 | | |
| WO | 2015103550 A1 | 7/2015 | | |
| WO | 2015/115709 A1 | 8/2015 | | |
| WO | 2016/051734 A1 | 4/2016 | | |

OTHER PUBLICATIONS

Xiao et al. "Ratiometric photoacoustic imaging of endoplasmic reticulum polarity in injured liver tissues of diabetic mice". Chem. Sci., 2017, 8, p. 7025-7030. (Year: 2017).*

Akinori Miyata et al: "Photoacoustic Tomography of Human Hepatic Malignancies Using Intraoperative Indocyanine Green Fluorescence Imaging", Plos One, vol. 9, Issue 11, Nov. 2014, pp. 1-8, (8 pages total).

Huang et al: "Non-invasive measurement of hepatic reserving function based on near-infrared spectroscopy", Tsinghua Tongfang Knowledge Network Technology Co., Ltd., pp. 1-4, (4 pages total), Jan. 2015.

Xin Liu et al: "Imaging of Indocyanine Green Perfusion in Mouse Liver With Fluorescence Diffuse Optical Tomography", IEEE Transactions on Biomedical Engineering, vol. 58, No. 8, pp. 2139-2143, (5 pages total), Aug. 2011.

Jinwoon Jung: "An Experiment Study for the Evaluation of the Photoacoustic Effect of Pectin-Melanin Admixture in the Subcutaneous Muscle Layer and Liver as a Long-retaining Inoculating Photoacoustic Contrast Agent", pp. 1-33, (42 pages total), Dec. 26, 2014.

Anil Khanal et al: "Microgel Encapsulated Methylene Blue for the Treatment of Breast Cancer Cells by Photodynamic Therapy", Journal of Breast Cancer,17(1), Mar. 2014, pp. 18-24. (7 pages total).

Xiaolan Feng et al: "Energy metabolism targeted drugs synergize with photodynamic therapy to potentiate breast cancer cell death", The Royal Society of Chemistry and Owner Societies, Photochem. Photobiol. Sci., 2014, p. 1793-1803, (11 pages total).

Ali Reza Montazerabadi et al: "The effects of combined treatment with ionizing radiation and indocyanine green-mediated photodynamic therapy on breast cancer cells", Journal of Photochemistry and Photobiology B: Biology 109, 2012, p. 42-49, (8 pages total).

Dan Wu et al: "Contrast Agents for Photoacoustic and Thermoacoustic Imaging: A Review", 2014, International Journal of Molecular Sciences , 15, ISSN 1422-0067, p. 23616-23639, (24 pages total).

Communication dated Mar. 12, 2018, issued by the European Patent Office in counterpart European Patent Application No. 17189251.6.

* cited by examiner

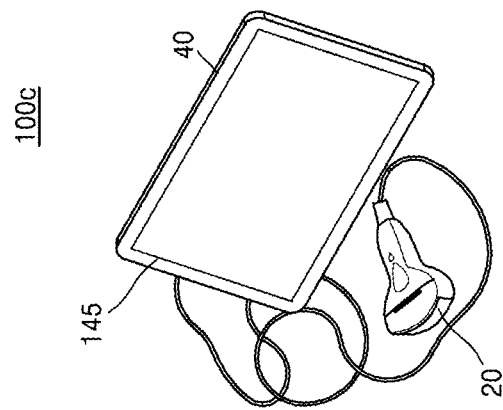
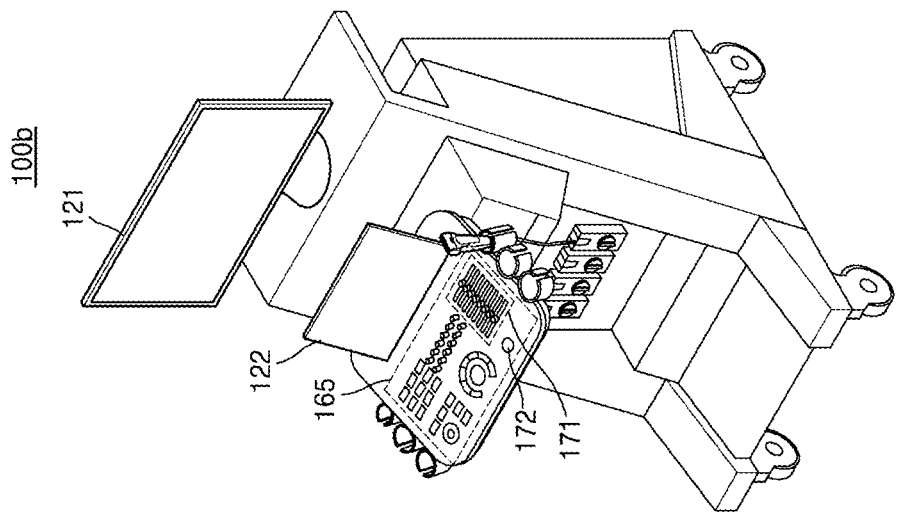
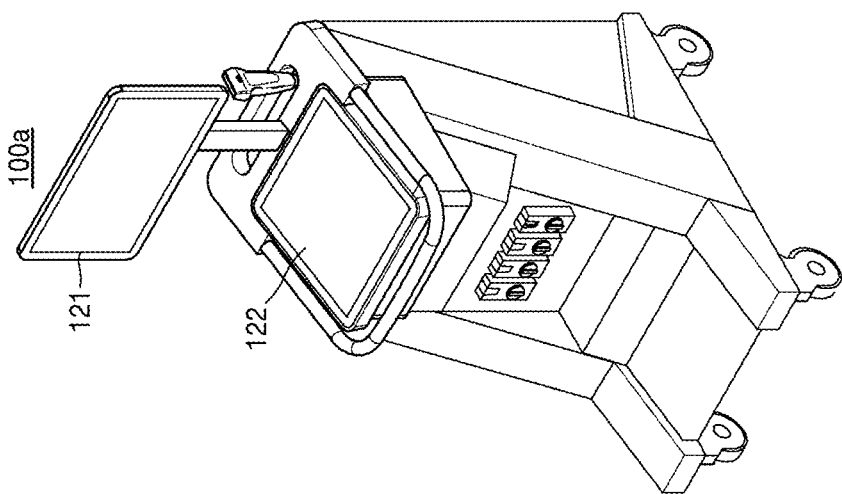

PHOTOACOUSTIC IMAGING DIAGNOSIS APPARATUS AND METHOD OF CONTROLLING THE SAME

CROSS-REFERENCE TO RELATED APPLICATION

This application claims the benefit of Korean Patent Application No. 10-2016-0179313, filed on Dec. 26, 2016, in the Korean Intellectual Property Office, the disclosure of which is incorporated herein in its entirety by reference.

BACKGROUND

1. Field

The present disclosure relates to diagnosis apparatuses using photoacoustic images and methods of controlling the diagnosis apparatuses.

2. Description of the Related Art

An invasive method has been used to determine whether an object is damaged. For example, an indocyanine green (ICG)-R15 test has been performed to determine whether the liver is damaged. The ICG-R15 test is a diagnosis method of determining liver damage, by administering ICG into a vein of a human body, and collecting blood samples every 5 minutes for 15 minutes to measure a concentration ratio of the ICG remaining in the blood vessel. However, the ICG-R15 test is accompanied with pain due to the gathering of blood. In addition, according to the ICG-R15 test, the collected blood has to be analyzed by a spectrophotometer to measure the ICG concentration in the blood, and thus, liver damage may not be determined in real-time. In addition, according to the invasive method of the related art, it may not be clearly determined whether the liver of a living donor is damaged.

To address the above problems, various medical imaging techniques have been researched to determine whether an object is damaged in real-time by using a noninvasive method.

For example, photoacoustic imaging technology is technology for noninvasively projecting biological tissue by using a photoacoustic effect. When a laser pulse is irradiated to biological tissue to generate a photoacoustic image, the biological tissue thermoelastically expands due to local heat accumulation. Thus, an ultrasound wave having a frequency of a wide band is generated from the biological tissue, and the ultrasound wave is detected by an ultrasound transducer. An image is generated using the detected ultrasound wave.

The photoacoustic imaging techniques have been studied at a considerable level, targeting tissues such as the brain, heart, and eye of an animal.

SUMMARY

Provided are photoacoustic imaging diagnosis apparatuses capable of providing information about a damage degree of an object in a noninvasive manner by using a photoacoustic image, and methods of controlling the photoacoustic imaging diagnosis apparatuses.

Provided are non-transitory computer-readable recording media having recorded thereon a program, which when executed by a computer, performs the above methods.

Additional aspects will be set forth in part in the description which follows and, in part, will be apparent from the description, or may be learned by practice of the presented embodiments.

According to an aspect of an embodiment, a method of controlling a photoacoustic imaging diagnosis apparatus, the method includes: irradiating to an object an optical signal having a wavelength corresponding to an optical energy absorption wavelength of a contrast medium that is injected to the object; receiving a photoacoustic signal generated from the object in response to the optical signal; generating scan information representing an intensity of the photoacoustic signal based on the photoacoustic signal; determining a damage degree of the object by using a variation in the intensity of the photoacoustic signal during a preset time period included in the scan information; and displaying the damage degree of the object.

According to an aspect of another embodiment, a non-transitory computer-readable recording medium has embodied thereon a program for executing the method of controlling the photoacoustic imaging diagnosis apparatus according to the above controlling method.

According to an aspect of another embodiment, a photoacoustic imaging diagnosis apparatus includes: an optical signal transmitter configured to irradiate to an object an optical signal having a wavelength corresponding to an optical energy absorption wavelength of a contrast medium that is injected to the object; an ultrasound probe configured to receive a photoacoustic signal generated from the object in response to the optical signal; at least one processor configured to generate scan information representing an intensity of the photoacoustic signal based on the photoacoustic signal, and determine a damage degree of the object by using a variation in the intensity of the photoacoustic signal during a preset time period included in the scan information; and a display configured to display the damage degree of the object.

BRIEF DESCRIPTION OF THE DRAWINGS

These and/or other aspects will become apparent and more readily appreciated from the following description of the embodiments, taken in conjunction with the accompanying drawings in which:

FIGS. 2A to 2C are diagrams of photoacoustic imaging diagnosis apparatuses, according to an embodiment;

DETAILED DESCRIPTION

Figure 1:
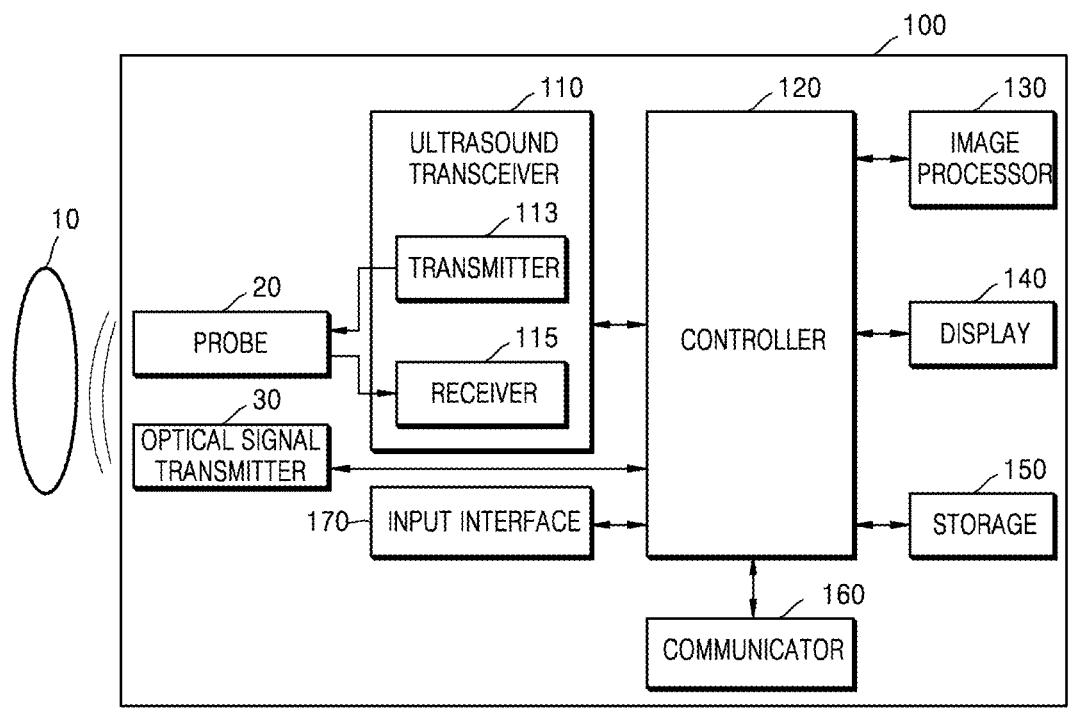
FIG. 1 is a block diagram of a photoacoustic imaging diagnosis apparatus according to an embodiment.

As used herein, the term "and/or" includes any and all combinations of one or more of the associated listed items. Expressions such as "at least one of," when preceding a list of elements, modify the entire list of elements and do not modify the individual elements of the list.

The present specification describes principles of the present disclosure and provides embodiments so that a scope of the present disclosure may be clarified and one of ordinary skill in the art would carry out the present disclosure. The embodiments may be implemented in various types.

Throughout the specification, like reference numerals denote the same elements. The present specification does not explain all of the elements of the embodiments, and content common in the technical field to which the present disclosure belongs or same content among the embodiments will be omitted. The term 'part' or 'portion' used herein may be implemented as software or hardware, and according to embodiments, a plurality of 'parts' may be implemented as one unit or element or one 'part' may include a plurality of units or elements. Hereinafter, operating principles of the present disclosure one or more embodiments of the present disclosure will be described in detail with reference to accompanying drawings.

In the present specification, images may include medical images obtained by a medical imaging apparatus such as a magnetic resonance imaging (MRI) apparatus, a computed tomography (CT) apparatus, an ultrasound imaging apparatus, an X-ray imaging apparatus, etc.

In the present specification, an 'object' is a target to be photographed, and may include a human body, an animal, or a part thereof. For example, an object may include a part of a body (organs) or phantoms.

Throughout the entire specification, an "ultrasound image" is an image about an object, the image is processed based on an ultrasound signal transmitted to the object and reflected by the object.

Throughout the entire specification, a 'photoacoustic image' is an image about an object, the image being processed based on a photoacoustic signal generated from the object, to which an optical signal is irradiated.

Hereinafter, one or more embodiments will be described below with reference to accompanying drawings.

FIG. 1 is a block diagram of a photoacoustic imaging diagnosis apparatus 100 according to an embodiment. The photoacoustic imaging diagnosis apparatus 100 according to the embodiment may include a probe 20, an optical signal transmitter 30, an ultrasound transceiver 110, a controller 120, an image processor 130, a display 140, a storage 150, and an input interface 170.

The photoacoustic imaging diagnosis apparatus 100 may be of a cart-type or a portable-type photoacoustic imaging diagnosis apparatus. Examples of a portable-type photoacoustic imaging diagnosis apparatus may include a smartphone, a laptop computer, a personal digital assistant (PDA), and a tablet personal computer (PC), each of which may include a probe and an application, but embodiments are not limited thereto.

The probe 20 may include a plurality of transducers. The plurality of transducers may transmit ultrasound signals to an object 10 in response to transmitting signals applied by a transmitter 113. The plurality of transducers may receive ultrasound signals reflected from the object 10 to generate reception signals. In addition, the probe 20 and the photoacoustic imaging diagnosis apparatus 100 may be formed in one body, or the probe 20 and the photoacoustic imaging diagnosis apparatus 100 may be separate but linked wirelessly or via wires. In addition, the photoacoustic imaging diagnosis apparatus 100 may include one or more probes 20 according to embodiments.

The optical signal transmitter 30 may generate an optical signal to be irradiated towards an object 10. Also, the optical signal transmitter 30 may irradiate the generated optical signal towards the object 10. The optical signal transmitter 30 may adjust a frequency of the optical signal to be irradiated, based on the object 10. The optical signal transmitter 30 may adjust the frequency of the optical signal to be irradiated, based on a contrast medium injected to the object 10. The optical signal transmitter 30 may adjust the frequency of the optical signal, so as to correspond to an optical energy absorption frequency of the contrast medium. The optical signal transmitter 30 may generate an optical signal having a frequency corresponding to the optical energy absorption frequency of the contrast medium, as illustrated with reference to Table 1 below.

TABLE 1

| Photoacoustic Contrast Agent | Type | Absorption Peak (nm) | Size (nm) | Modification Application | Application |
|---|---|---|---|---|---|
| Indocyanine-green | NIR Fluorescent Dye | 810 | <2 | CarbonNanotube, PEG, PEBBLEs | PAT, in tissue phantoms and in vivo |
| Methylene blue | NIR Fluorescent Dye | 650-700 | <2 | | PAT, in tissue phantoms |

TABLE 1-continued

| Photoacoustic Contrast Agent | Type | Absorption Peak (nm) | Size (nm) | Modification Application | Application |
|---|---|---|---|---|---|
| Alexa Fluor 750 | NIR Fluorescent Dye | 750 | <2 | | Multispectral PAI, in vivo |
| IRDye800CW | NIR Fluorescent Dye | 750-800 | <2 | NPR-1 | PAS, in vivo |
| IRDye800-c(KRGDf) | NIR Fluorescent Dye | 750-790 | <2 | Integral protein$\alpha v\beta 3$ | PAS, in vivo |
| Evans Blue | NIR Fluorescent Dye | 550 | <2 | | PAT, in vivo |
| PPCy-C8 | NIR Fluorescent Dye | 754-789 | <2 | Perfluorocarbon | In vivo, dual-modality PAI-FI |
| Cypate-C18 | NIR Fluorescent Dye | 754-790 | <2 | Perfluorocarbon | In vivo, dual-modality PAI-FI |
| Caspase-9 Probe | NIR Fluorescent Dye | 640 | <2 | | PAI, in vivo |
| MMPSence ™ 680 | NIR Fluorescent Dye | 620, 680 | <2 | | PAI, in tissue phantoms |
| BHQ3 | Quencher | 672 | <2 | | PAI, in vitro |
| QXL680 | Quencher | 680 | <2 | | PAI, in vitro |
| Au Nanospheres | Plasmonic Noble Metal Nanoparticle | 520-550 | 20-80 | PEG | PAT, in vivo |
| Au Nanoshells | Plasmonic Noble Metal Nanoparticle | 700-1100 | 50-500 | PEG | PAT, in vivo |
| Au Nanorods | Plasmonic Noble Metal Nanoparticle | 550-1550 | a few to hundreds of | HER2, EGFR | PAI, in vitro |
| Au Nanocages | Plasmonic Noble Metal Nanoparticle/ Theranostic Contrast Agent | 820 | 25 | | PAT, in vivo, photothermal therapy |
| Au Nanoclusters | Plasmonic Noble Metal Nanoparticle | 500-550 | 100 | | PAI, in vitro |
| Au Nanostars | Plasmonic Noble Metal Nanoparticle | 767 | 120 | | PAT, in vivo |
| Au Nanobeacons | Plasmonic Noble Metal Nanoparticle | 520 | 150 | $\alpha,\beta_3$ | PAT, in vivo |
| Ag Nanoplates | Plasmonic Noble Metal Nanoparticle | 550-1080 | 25-218 | a-EGFR, PEG | PAI, in vivo |
| Ag Nanosystems | Plasmonic Noble Metal Nanoparticle/ Theranostic Contrast Agent | 400-500 | 180-520 | | PAI, ex vivo; image-guided therapy |
| Quantum dots | Nanoparticles Based On Other Principles | 400-750 | <10 | | PAT, in vivo: Triple-modality PA-PT-Fluorescent |
| Nanodiamond | Nanoparticles Based On Other Principles | 820 | 68.7 | | PAI, in vivo |
| Polypyrrole Nanoparticles | Nanoparticles Based On Other Principles | 700-900 | 46 | | PAI, in vivo |
| Copper Sulfide | Nanoparticles Based On Other Principles | 900 | 11 ± 3 | | PAI, in vivo |
| Graphene Nanosheets | Nanoparticles Based On Other Principles | 200-900 | 10 | | PAI, in vivo |
| Iron Oxide-gold Core-shell | Multimodality Contrast Agent | 660-900 | 1-5 | | Triple-modality MRI-PAI-mmPA |
| Gd$_2$O$_3$ | Multimodality Contrast Agent | | 100 | DEG, gelatin | In vivo, dual-modality PAT-MRI |
| Single-walled Carbon Nanotubes (SWNT) | Multimodality Contrast Agent | 785 | 5-8 | Protamine, PEG | In vivo, Triple-modality Raman- MRI-PAI |
| Dye-loaded Perfluorocarbon-based Nanoparticles | Multimodality Contrast Agent | 750-800 | 220 ± 11 | cypate-C18, PPCy-C8, PEG2000, phosphatidylethanolamine | In vivo, dual-modality PAI-FI |

TABLE 1-continued

| Photoacoustic Contrast Agent | Type | Absorption Peak (nm) | Size (nm) | Modification Application | Application |
|---|---|---|---|---|---|
| AuMBs | Multimodality Contrast Agent | 760 | 100-1000 | HAS | Dual-modality PAI-UI |
| Triggered Nanodroplets | Multimodality Contrast Agent | 750-800 | 300 | Perfluorocarbon | In tissue phantoms and in vivo, dual-modality PAT-UI |
| Cobalt Nanowontons | Multimodality Contrast Agent | 700 | 30-90 | | Dual-modality MRI-PAT |
| Nanoroses | Multimodality Contrast Agent | 700-850 | 30 | | PAI, in vitro |
| MPRs | Theranostic/ Multimodality Contrast Agent | 532 | 120 | maleimide-DOTA-Gd | In vivo, triple-modality MRI-API-Raman; image-guided surgery |
| Goldsilica Core shell Nanorods | Theranostic Contrast Agent | 780 | 10.3 ± 1.1 | PEG | PAI, in vitro |
| Superparamagnetic Iron Oxide (SPIO) | Theranostic Contrast Agent | 500-780 | 80-150 | | PAI, ex vivo |

According to an embodiment, the optical signal transmitter 30 may generate an optical signal having a frequency of 1.2 MHz corresponding to the optical energy absorption wavelength of indocyanine green (IGC), e.g., 840 nm, and then, may irradiate the generated optical signal to the object 10.

According to the embodiment, the optical signal transmitter 30 may be included in the probe 20. According to another embodiment, the optical signal transmitter 30 may be attached to/detached from the probe 20.

The controller 120 may control the transmitter 113 to generate transmission signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analog to digital signals and summing the digital reception signals based on a position and a focal point of the plurality of transducers.

The controller 120 may control an ultrasound receiver 115 to generate photoacoustic data, by performing an analog/digital conversion of a photoacoustic signal transmitted from the probe 20, and combining received signals that are digitally converted by taking into account locations of a plurality of transducers and focusing points.

The image processor 130 may generate an ultrasound image by using ultrasound data generated from the ultrasound receiver 115. The image processor 130 may generate a photoacoustic image by using the photoacoustic data generated by the ultrasound receiver 115.

The controller 120 and the image processor 130 may be implemented as one processor, or may be each implemented as one or more processors. The processor may be implemented as an array of a plurality of logic gates, or as a combination of a universal microprocessor and a memory storing programs that may be executed by the microprocessor. In addition, one of ordinary skill in the art would appreciate that the central processor may be implemented as other types of hardware.

The display 140 may display the generated ultrasound image, the photoacoustic image, and various information processed by the photoacoustic imaging diagnosis apparatus 100. The photoacoustic imaging diagnosis apparatus 100 may include two or more displays 140 according to embodiments. The display 140 may include a touch screen in combination with a touch panel.

The controller 120 may control the operations of the photoacoustic imaging diagnosis apparatus 100 and flow of signals between the internal elements of the photoacoustic imaging diagnosis apparatus 100. The controller 120 may include a memory for storing a program or data to perform functions of the photoacoustic imaging diagnosis apparatus 100 and a processor and/or a microprocessor (not shown) for processing the program or data. For example, the controller 120 may control the operation of the photoacoustic imaging diagnosis apparatus 100 by receiving a control signal from the input interface 170 or an external apparatus.

The photoacoustic imaging diagnosis apparatus 100 may include a communicator 160 and may be connected to external apparatuses, for example, servers, medical apparatuses, and portable devices such as smart phones, tablet PCs, wearable devices, etc., via the communicator 160.

The communicator 160 may include at least one element capable of communicating with the external apparatus. For example, the communicator 160 may include at least one of a short-range communication module, a wired communication module, and a wireless communication module.

The communicator 160 may receive a control signal and data from an external apparatus and transmit the received control signal to the controller 120, so that the controller 120 may control the photoacoustic imaging diagnosis apparatus 100 in response to the received control signal.

The controller 120 may transmit a control signal to an external apparatus via the communicator 160 so that the external apparatus may be controlled in response to the control signal of the controller 120.

For example, the external apparatus connected to the ultrasound diagnosis apparatus 100 may process data of the external apparatus in response to control signal of the controller 120 received via the communicator 160.

A program for controlling the photoacoustic imaging diagnosis apparatus 100 may be installed in the external apparatus. The program may include command languages to perform part of the operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the photoacoustic imaging diagnosis apparatus 100, input and/or output ultrasound data, ultrasound images, applications, etc.

The storage 150 may store a kind of the contrast medium injected to the object 10, a wavelength at which the contrast medium may absorb the optical energy at most, and a frequency of an optical signal corresponding to the wavelength.

The controller 120 may control the optical signal irradiated by the optical signal transmitter 30 by using a kind of the contrast medium, a wavelength at which the contrast medium may absorb the optical energy at most, and a frequency of an optical signal corresponding to the wavelength.

The storage 150 may store preset values related to a damage degree of the object 10. The storage 150 may store preset values related to a damage degree of each of a plurality of regions of the object 10. The storage 150 may store information about preset colors corresponding to the preset values. The storage 150 may store an excision target region of the object 10, corresponding to the preset values. The storage 150 may store a location for an excision procedure corresponding to the excision target region of the object 10 corresponding to the preset values.

The input interface 170 may receive a user's input to control the photoacoustic imaging diagnosis apparatus 100 and may include a key pad, buttons, a keypad, a mouse, a trackball, a jog switch, a knob, a touchpad, a touch screen, a microphone, motion input means, biometrics input means, etc. For example, the user's input may include inputs manipulating buttons, keypads, mice, track balls, jog switches, or knobs, inputs touching a touchpad or a touch screen, a voice input, a motion input, and a bioinformation input, for example, iris recognition or fingerprint recognition, but an exemplary embodiment is not limited thereto.

The input interface 170 may receive a user's input for setting a region of interest.

An example of the photoacoustic imaging diagnosis apparatus 100 according to the embodiment will be described later with reference to FIGS. 2A to 2C.

FIGS. 2A to 2C are diagrams of photoacoustic imaging diagnosis apparatuses 100a and 100b according to an embodiment.

Referring to FIGS. 2A and 2B, the photoacoustic imaging diagnosis apparatuses 100a and 100b may respectively include a main display 121 and a sub-display 122. One of the main display 121 and the sub-display 122 may be implemented as a touch screen. The main display 121 and the sub-display 122 may display ultrasound images and various information processed by the photoacoustic imaging diagnosis apparatuses 100a and 100b. In addition, the main display 121 and the sub-display 122 may be implemented as touch screens providing a graphical user interface (GUI), thereby receiving data for controlling the photoacoustic imaging diagnosis apparatuses 100a and 100b from a user. For example, the main display 121 may display an ultrasound image, and the sub-display 122 may display a control panel for controlling the display of the ultrasound image as a GUI. The sub-display 122 may receive data for controlling the display of the image via the control panel represented as the GUI. The photoacoustic imaging diagnosis apparatuses 100a and 100b may control the display of the ultrasound image on the main display 121 by using the received data.

Referring to FIG. 2B, the photoacoustic imaging diagnosis apparatus 100b may further include a control panel 165, in addition to the main display 121 and the sub-display 122. The control panel 165 may include a button, a track ball, a jog switch, a knob, etc., and may receive data for controlling the photoacoustic imaging diagnosis apparatus 100b from the user. For example, the control panel 165 may include a time gain compensation (TGC) button 171, a freeze button 172, etc. The TGC button 171 is a button for setting a TGC value according to a depth of the ultrasound image. In addition, when sensing an input through the freeze button 172, the photoacoustic imaging diagnosis apparatus 100b may maintain a status of displaying a frame image at a corresponding time point.

In addition, the button, the track ball, the jog switch, the knob, etc. included in the control panel 165 may be provided as the GUI on the main display 121 or the sub-display 122.

Referring to FIG. 2C, a photoacoustic imaging diagnosis apparatus 100c may be implemented being portable. Examples of the photoacoustic imaging diagnosis apparatus 100c may include a smart phone including a probe and applications, a laptop computer, a PDA, a tablet PC, etc., but are not limited thereto.

The photoacoustic imaging diagnosis apparatus 100c may include the probe 20 and a main body 40, and the probe 20 may be connected through wires or wirelessly to a side of the main body 40. The main body 40 may include a touch screen 145. The touch screen 145 may display the ultrasound image, and various information processed by the ultrasound diagnosis apparatus, and the GUI.

Figure 3:
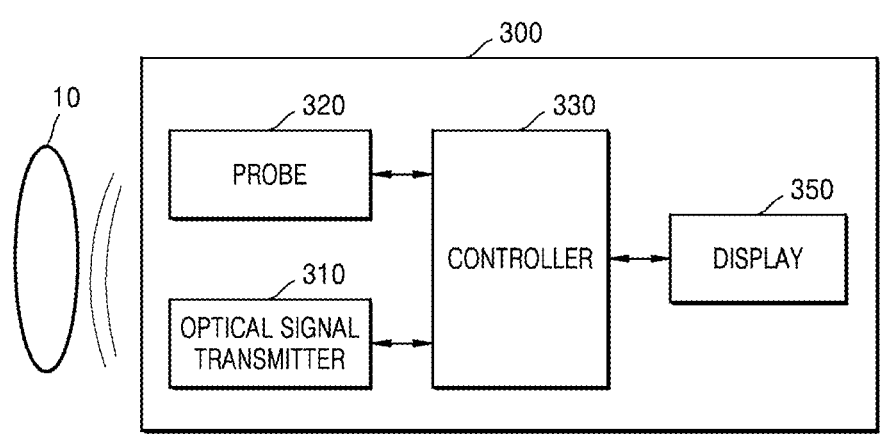
FIG. 3 is a block diagram of a photoacoustic imaging diagnosis apparatus according to an embodiment.

FIG. 3 is a block diagram of a photoacoustic imaging diagnosis apparatus according to an embodiment.

According to an embodiment illustrated with reference to FIG. 3, the photoacoustic imaging diagnosis apparatus 300 may include an optical signal transmitter 310, a probe 320, a controller 330, and a display 350.

The optical signal transmitter 310 may generate an optical signal to be irradiated to the object 10. The optical signal transmitter 310 may irradiate the optical signal to the object 10. The optical signal transmitter 310 may adjust a frequency of the optical signal that is to be irradiated, based on the object 10. The optical signal transmitter 310 may adjust the frequency of the optical signal to be irradiated, based on a contrast medium injected to the object 10. The optical signal transmitter 310 may adjust the frequency of the optical signal, so as to correspond to an optical energy absorption frequency of the contrast medium. The optical energy absorption wavelength of the contrast medium and the corresponding frequency of the optical signal are illustrated above in Table 1.

According to an embodiment, the optical signal transmitter 310 may generate an optical signal having a frequency of 1.2 MHz corresponding to the optical energy absorption wavelength of IGC, e.g., 840 nm, and then, may irradiate the generated optical signal to the object 10.

According to the embodiment, the optical signal transmitter 310 may be included in the probe 320, or may be separately provided from the probe 320 and attached to the probe 320.

The probe 320 may include a plurality of transducers. The plurality of transducers may transmit ultrasound signals to the object 10. The plurality of transducers receive the ultrasound signals reflected by the object 10 or the photoacoustic signal generated from the object 10, and form reception signals.

The controller 330 may include at least one processor. The controller 330 may control each of the components included in the photoacoustic imaging diagnosis apparatus 300. The controller 330 may generate a photoacoustic image by using the photoacoustic data transmitted from the probe 320. The controller 330 may generate an ultrasound image by using the ultrasound data transmitted from the probe 320.

According to an embodiment, the controller 330 may control the optical signal transmitter 310 to change a frequency of the optical signal generated by the optical signal transmitter 310. The controller 330 may control an intensity of the optical signal irradiated from the optical signal transmitter 310 to the object 10, and an irradiation time of the optical signal.

According to the embodiment, the controller 330 may control the probe 320 to generate ultrasound data or photoacoustic data by performing analog-digital conversion of the signal transmitted from the probe 320 and combining the digitally converted signals based on locations of the plurality of transducers and focusing points.

According to an embodiment, the controller 330 may generate scan information representing an intensity of the photoacoustic signal by using the photoacoustic signal. The controller 330 may generate photoacoustic data by using the photoacoustic signal, and may generate scan data representing the intensity of the photoacoustic signal by using the photoacoustic data.

According to an embodiment, the controller 330 may determine a damage degree of the object 10 based on a variation in the photoacoustic signal received for a predetermined time period, by using the scan information.

According to an embodiment, the controller 330 may determine a damage degree of the liver based on a variation in the photoacoustic signal transmitted from the liver of a human body during a predetermined time period.

According to an embodiment, the controller 330 may determine the damage degree of the liver based on the variation in the intensity of the photoacoustic signal transmitted from the liver for 15 minutes from a time point of administering the ICG.

The display 350 may display the damage degree of the object 10.

According to an embodiment, the display 350 may display a damage value that is obtained by digitizing the damage degree of the object 10.

According to an embodiment, the display 350 may display the damage degree of the object 10 by using the photoacoustic image and a time intensity curve (TIC) of the object 10.

According to an embodiment, the display 350 may display the damage degree of the object 10 by using the color-coded photoacoustic image.

According to an embodiment, the display 350 may display the damage degree of the object 10 by using the photoacoustic image of the object 10 and the ultrasound image of the object 10.

According to an embodiment, the display 350 may display the damage degree of the object 10 by overlaying the photoacoustic image of the object 10 on the ultrasound image of the object 10.

According to an embodiment, the display 350 may display the damage degree of the object 10 by using the ultrasound image that is color-coded.

The photoacoustic imaging diagnosis apparatus 300 may provide information about the damage degree of the object 10 in real-time in a noninvasive manner. For example, the photoacoustic imaging diagnosis apparatus 300 may provide information about the damage degree of the liver in real-time. The photoacoustic imaging diagnosis apparatus 300 may provide the information about the damage degree of the liver in real-time, by determining a liver reserve function. The photoacoustic imaging diagnosis apparatus 300 may provide information about the damage degree of the liver of a patient who needs to get a hepatic resection. The photoacoustic imaging diagnosis apparatus 300 may provide information of the damage degree of the liver of a living donor in real-time.

Figure 4:
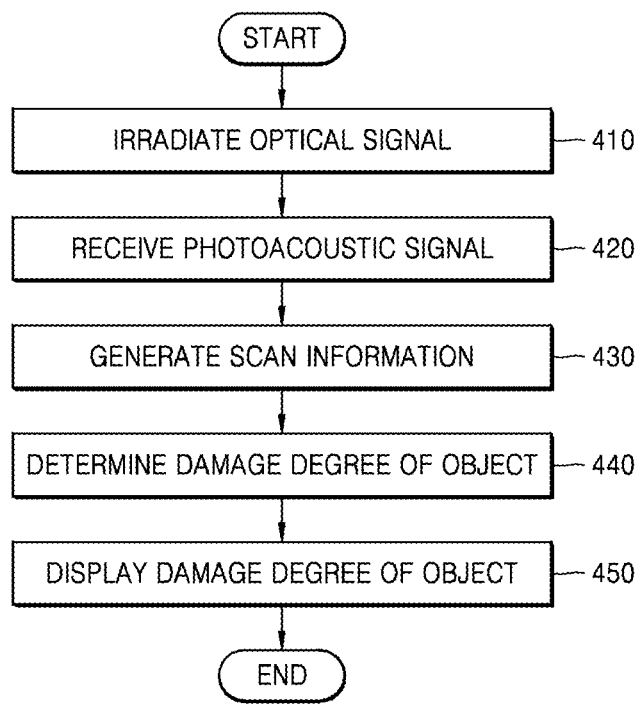
FIG. 4 is a flowchart illustrating a method of controlling a photoacoustic imaging diagnosis apparatus, according to an embodiment.

FIG. 4 is a flowchart illustrating a method of controlling a photoacoustic imaging diagnosis apparatus, according to an embodiment.

Referring to FIG. 4, the method of controlling a photoacoustic imaging diagnosis apparatus may include irradiating an optical signal (410), receiving a photoacoustic signal (420), generating scan information (430), determining a damage degree of an object (440), and displaying the damage degree of the object (450).

In operation 410, the photoacoustic imaging diagnosis apparatus 300 may generate and irradiate an optical signal to the object 10. The photoacoustic imaging diagnosis apparatus 300 may adjust a frequency of the optical signal to be irradiated based on the object 10 or the contrast medium injected to the object 10.

According to an embodiment, the photoacoustic imaging diagnosis apparatus 300 may generate the optical signal having the frequency corresponding to the optical energy absorption wavelength of the contrast medium injected to the object 10, as illustrated in Table 1. The photoacoustic imaging diagnosis apparatus 300 may irradiate to the object 10 the optical signal having the frequency corresponding to the optical energy absorption wavelength of the contrast medium injected to the object 10.

According to an embodiment, the photoacoustic imaging diagnosis apparatus 300 may generate an optical signal having a frequency of 1.2 MHz corresponding to the optical energy absorption wavelength of the ICG that is injected to the liver, e.g., 840 nm. The photoacoustic imaging diagnosis apparatus 300 may irradiate the optical signal having a frequency of 1.2 MHz to the liver.

In operation 420, the photoacoustic imaging diagnosis apparatus 300 may receive a photoacoustic signal generated by the object 10. The photoacoustic imaging diagnosis apparatus 300 receives the photoacoustic signal generated by the object 10 that is thermally expanded by the irradiated optical signal, and forms a reception signal.

According to an embodiment, the photoacoustic imaging diagnosis apparatus 300 may receive the photoacoustic signal generated, by the optical signal, from the contrast medium injected to the object 10, and may form the reception signal.

In operation 430, the photoacoustic imaging diagnosis apparatus 300 may generate scan information representing the intensity of the photoacoustic signal by using the photoacoustic signal. For example, the photoacoustic imaging diagnosis apparatus 300 may generate scan information representing the intensity of the photoacoustic signal generated by the ICG that has been injected to the liver.

According to an embodiment, the photoacoustic imaging diagnosis apparatus 300 may generate scan information including an average value of the intensity of the received photoacoustic signal. For example, the photoacoustic imaging diagnosis apparatus 300 may generate scan information including an average value of the intensity of the photoacoustic signal generated by the ICG injected to the liver.

According to an embodiment, the photoacoustic imaging diagnosis apparatus 300 may generate scan information including information related to accumulated intensity of the received photoacoustic signal according to time. For example, the photoacoustic imaging diagnosis apparatus 300 may generate scan information including information about the accumulated intensity of the photoacoustic signal generated by the ICG injected to the liver, according to time.

According to an embodiment, the photoacoustic imaging diagnosis apparatus 300 may generate scan information including information about the intensity of the photoacoustic signal with respect to each of the plurality of regions of the object 10. For example, the photoacoustic imaging diagnosis apparatus 300 may generate the scan information including information about the intensity of the photoacoustic signal generated from each of the plurality of regions of the liver.

In operation 440, the photoacoustic imaging diagnosis apparatus 300 may determine the damage degree of the object 100 based on the variation in the intensity of the photoacoustic signal during a preset time period included in the generated scan information.

According to an embodiment, the photoacoustic imaging diagnosis apparatus 300 may determine the damage degree of the object 10 based on the variation in the intensity of the photoacoustic signal. For example, the photoacoustic imaging diagnosis apparatus 300 may determine the damage degree of the liver based on the variation in the intensity of the photoacoustic signal transmitted from the ICG injected to the liver.

According to an embodiment, the photoacoustic imaging diagnosis apparatus 300 may determine the damage degree of the object 10 based on the variation of the photoacoustic signal during a preset time period, the variation being extracted from the accumulated intensity of the photoacoustic signal according to time. For example, the photoacoustic imaging diagnosis apparatus 300 may determine the damage degree of the liver based on the variation in the photoacoustic signal during the preset time period, the variation being extracted from the accumulated intensity of the photoacoustic signal transmitted from the ICG injected to the liver according to time.

According to an embodiment, the photoacoustic imaging diagnosis apparatus 300 may determine the damage degree of the object 10 based on an average value of the intensities of the photoacoustic signal. For example, the photoacoustic imaging diagnosis apparatus 300 may determine the damage degree of the liver based on the average value of the intensities of the photoacoustic signal transmitted from the ICG injected to the liver.

According to an embodiment, the photoacoustic imaging diagnosis apparatus 300 may determine the damage degree of each of the plurality of regions of the object 10, based on the variation in the intensity of the photoacoustic signal transmitted from each of the plurality of regions of the object 10. For example, the photoacoustic imaging diagnosis apparatus 300 may determine the damage degree of each of the plurality of regions of the liver, based on the variation in the intensity of the photoacoustic signal transmitted from each of the plurality of regions in the liver.

According to an embodiment, the photoacoustic imaging diagnosis apparatus 300 may determine the damage degree of the liver, based on the variation in the intensity of the photoacoustic signal transmitted from the liver for 15 minutes after the administration of the ICG.

According to an embodiment, the photoacoustic imaging diagnosis apparatus 300 may determine the damage degree of the liver, based on the variation in an intensity ratio of the photoacoustic signal transmitted from the liver for 15 minutes after the administration of the ICG.

In operation 450, the photoacoustic imaging diagnosis apparatus 300 may display the damage degree of the object 10.

According to the embodiment, the photoacoustic imaging diagnosis apparatus 300 may display the damage value that is obtained by digitizing the damage degree of the object 10.

According to an embodiment, the photoacoustic imaging diagnosis apparatus 300 may display the damage degree of the object 10 by using the photoacoustic image and a TIC of the object 10.

According to an embodiment, the photoacoustic imaging diagnosis apparatus 300 may display the damage degree of the object 10 by using a color-coded photoacoustic image.

According to an embodiment, the photoacoustic imaging diagnosis apparatus 300 may display the damage degree of the object 10 by using the photoacoustic image of the object 10 and an ultrasound image of the object 10.

According to an embodiment, the photoacoustic imaging diagnosis apparatus 300 may display the damage degree of the object 10 by overlaying the photoacoustic image of the object 10 on the ultrasound image of the object 10.

According to an embodiment, the photoacoustic imaging diagnosis apparatus 300 may display the damage degree of the object 10 by using an ultrasound image that is color-coded.

The photoacoustic imaging diagnosis apparatus 300 may provide information about the damage degree of the object 10 in real-time in a noninvasive manner. For example, the photoacoustic imaging diagnosis apparatus 300 may provide information about the damage degree of the liver in real-time. The photoacoustic imaging diagnosis apparatus 300 may provide the information about the damage degree of the liver in real-time, by determining a liver reserve function. The photoacoustic imaging diagnosis apparatus 300 may provide information about the damage degree of the liver of a patient who needs to get a hepatic resection. The photoacoustic imaging diagnosis apparatus 300 may provide information of the damage degree of the liver of a living donor in real-time.

Figure 5:
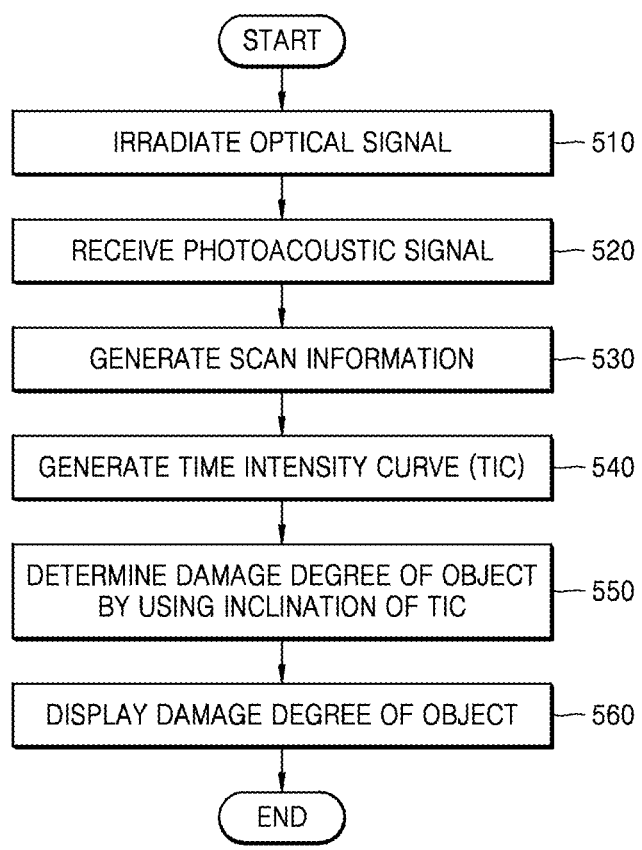
FIG. 5 is a flowchart illustrating a method of controlling a photoacoustic imaging diagnosis apparatus, according to an embodiment.
Figure 6:
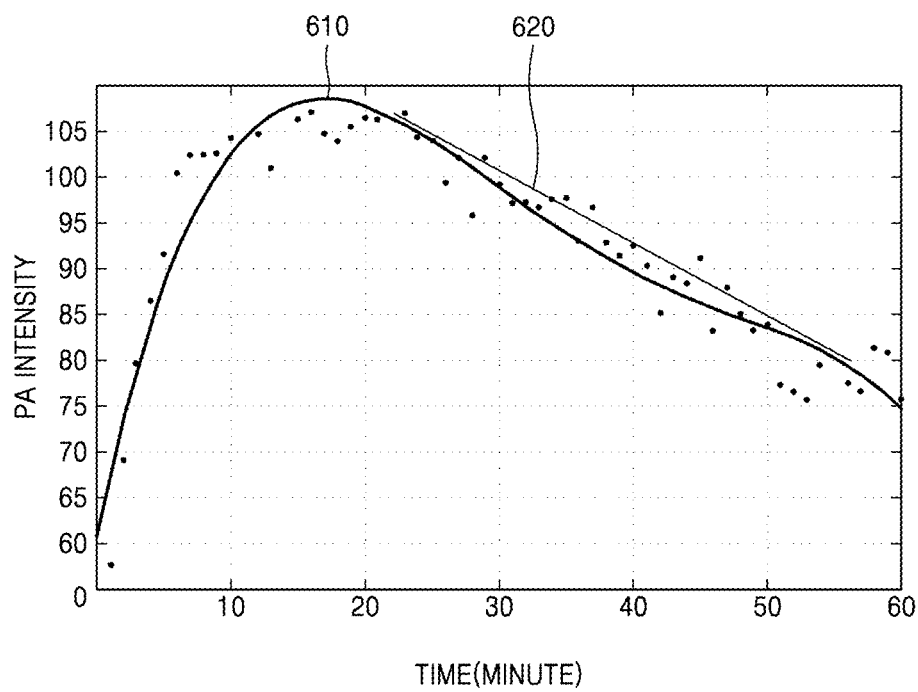
FIG. 6 is a graph showing a time intensity curve (TIC) representing a damage degree of an object, according to an embodiment.
Figure 7:
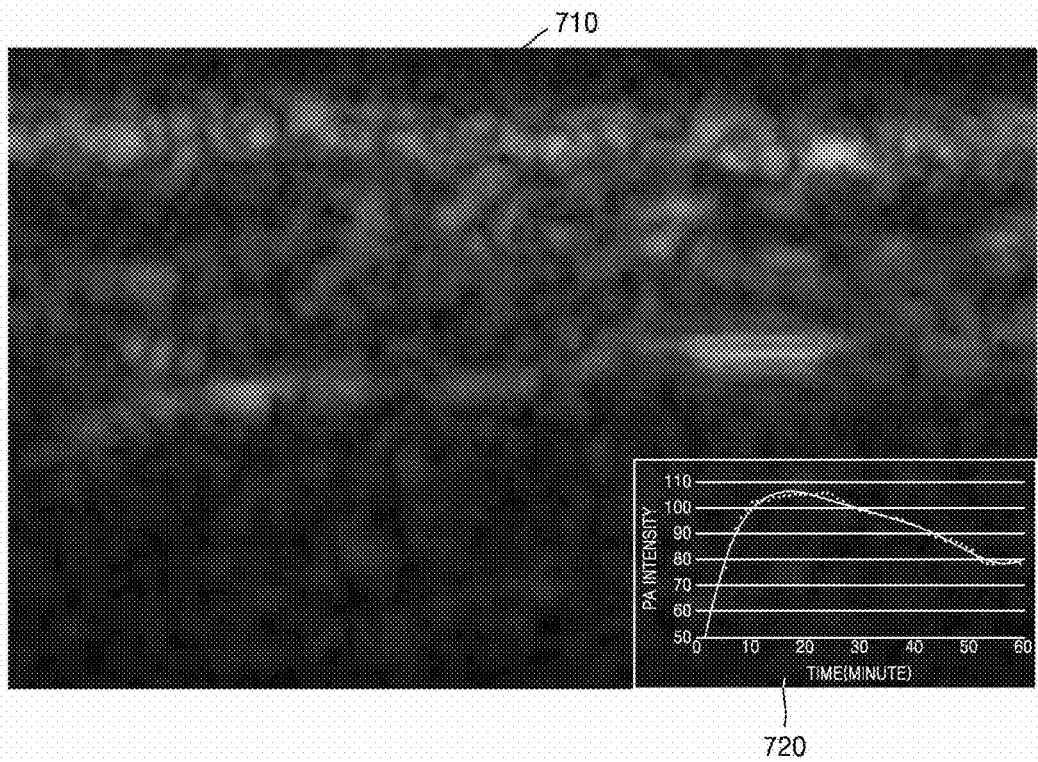
FIG. 7 is a diagram of a photoacoustic image and TIC according to an embodiment.

FIG. 5 is a flowchart illustrating a method of controlling a photoacoustic imaging diagnosis apparatus, according to an embodiment, FIG. 6 is a graph of a TIC for representing a damage degree of an object, according to an embodiment, and FIG. 7 is a diagram of a photoacoustic image and a TIC according to an embodiment.

According to the embodiment illustrated with reference to FIG. 5, the method of controlling a photoacoustic imaging diagnosis apparatus may include irradiating an optical signal (510), receiving a photoacoustic signal (520), generating scan information (530), generating a TIC (540), determining a damage degree of the object 10 by using an inclination of the TIC (550), and displaying the damage degree of the object 10 (560).

Operation 510 is similar to operation 410, and detailed descriptions thereof are omitted.

Operation 520 is similar to operation 420, and detailed descriptions thereof are omitted.

Operation 530 is similar to operation 430, and detailed descriptions thereof are omitted.

In operation 540, the photoacoustic imaging diagnosis apparatus 300 may generate a TIC representing an intensity of the photoacoustic signal according to time, by using generated scan information.

According to an embodiment, the photoacoustic imaging diagnosis apparatus 300 may generate a TIC 610 as shown in FIG. 6.

According to an embodiment, the photoacoustic imaging diagnosis apparatus 300 may generate a TIC representing a variation in intensity of the photoacoustic signal according to time, the photoacoustic signal being transmitted from the object 10. For example, the photoacoustic imaging diagnosis apparatus 300 may generate a TIC representing a variation versus time in intensity of the photoacoustic signal transmitted from the ICG injected to the liver.

According to an embodiment, the photoacoustic imaging diagnosis apparatus 300 may generate a TIC representing an accumulated intensity of the photoacoustic signal according to time, the photoacoustic signal being transmitted from the object 10. For example, the photoacoustic imaging diagnosis apparatus 300 may generate a TIC representing an accumulated intensity of the photoacoustic signal transmitted from the ICG injected to the liver, according to time.

According to an embodiment, the photoacoustic imaging diagnosis apparatus 300 may generate a TIC representing an average value of the intensity of the photoacoustic signal. For example, the photoacoustic imaging diagnosis apparatus 300 may generate a TIC representing an average value of the intensity of the photoacoustic signal transmitted from the ICG injected to the liver.

According to an embodiment, the photoacoustic imaging diagnosis apparatus 300 may generate a TIC with respect to each of a plurality of regions of the object 10, based on the variation in the intensity of the photoacoustic signal transmitted from each of the plurality of regions of the object 10. For example, the photoacoustic imaging diagnosis apparatus 300 may generate the TIC representing the variation versus time in the intensity of the photoacoustic signal transmitted from each of the plurality of regions of the liver.

In operation 550, the photoacoustic imaging diagnosis apparatus 300 may determine the damage degree of the object 10 by using an inclination of the generated TIC.

According to an embodiment, the photoacoustic imaging diagnosis apparatus 300 may determine the damage degree of the object 10 by using an inclination of the generated TIC during a preset time period. For example, the photoacoustic imaging diagnosis apparatus 300 may determine the damage degree of the object 10 by using the inclination of the TIC for 15 minutes after the administration of the ICG.

In operation 560, the photoacoustic imaging diagnosis apparatus 300 may display the damage degree of the object 10.

According to an embodiment, the photoacoustic imaging diagnosis apparatus 300 may display the damage degree of the object 10 by using the TIC and the inclination of the TIC during a preset time period. For example, as shown in FIG. 6, the photoacoustic imaging diagnosis apparatus 300 may display the damage degree of the liver by using the TIC 610 of the ICG injected to the liver and an inclination 620 of the TIC 610 for a preset time period. As another example, the photoacoustic imaging diagnosis apparatus 300 may display the damage degree of the liver by using the TIC of the ICG injected to the liver and the inclination of the TIC for 15 minutes after the administration of the ICG.

According to an embodiment, the photoacoustic imaging diagnosis apparatus 300 may display the damage degree of the object 10 by using the photoacoustic image and the TIC of the object 10. For example, as shown in FIG. 7, the photoacoustic imaging diagnosis apparatus 300 may display the damage degree of the liver by using a photoacoustic image of the liver and a TIC 720 of the liver. The photoacoustic imaging diagnosis apparatus 300 may display the damage degree of the liver of the photoacoustic image and the TIC of the ICG injected to the liver.

According to an embodiment, the photoacoustic imaging diagnosis apparatus 300 may display the damage degree of the object 10 by displaying both a TIC generated based on a photoacoustic signal generated from an object in a normal state and a TIC generated based on a photoacoustic signal transmitted from the object 10.

According to an embodiment, the photoacoustic imaging diagnosis apparatus 300 may display the damage degree of the object 10, by displaying both an inclination of the TIC generated based on the photoacoustic signal transmitted from an object in a normal state and an inclination of the TIC generated based on the photoacoustic signal transmitted from the object 10 in a damaged state.

According to an embodiment, the photoacoustic imaging diagnosis apparatus 300 may display the damage degree of the object 10 by using an inclination value of the TIC of the object 10. For example, the photoacoustic imaging diagnosis apparatus 300 may display the damage degree of the object 10 by displaying both an inclination value of the TIC of the object 10 and an inclination value of a TIC of the object in a normal state. As another example, the photoacoustic imaging diagnosis apparatus 300 may display the damage degree of the object 10 by displaying both an inclination value of the TIC of the object 10 and a critical inclination value that is set in advance.

Figure 8:
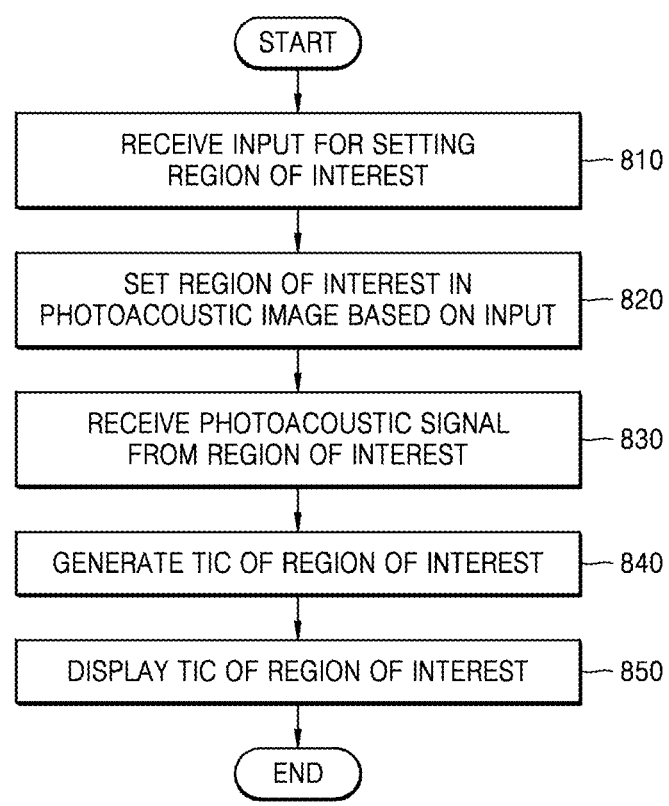
FIG. 8 is a flowchart illustrating a method of controlling a photoacoustic imaging diagnosis apparatus, according to an embodiment.
Figure 9:
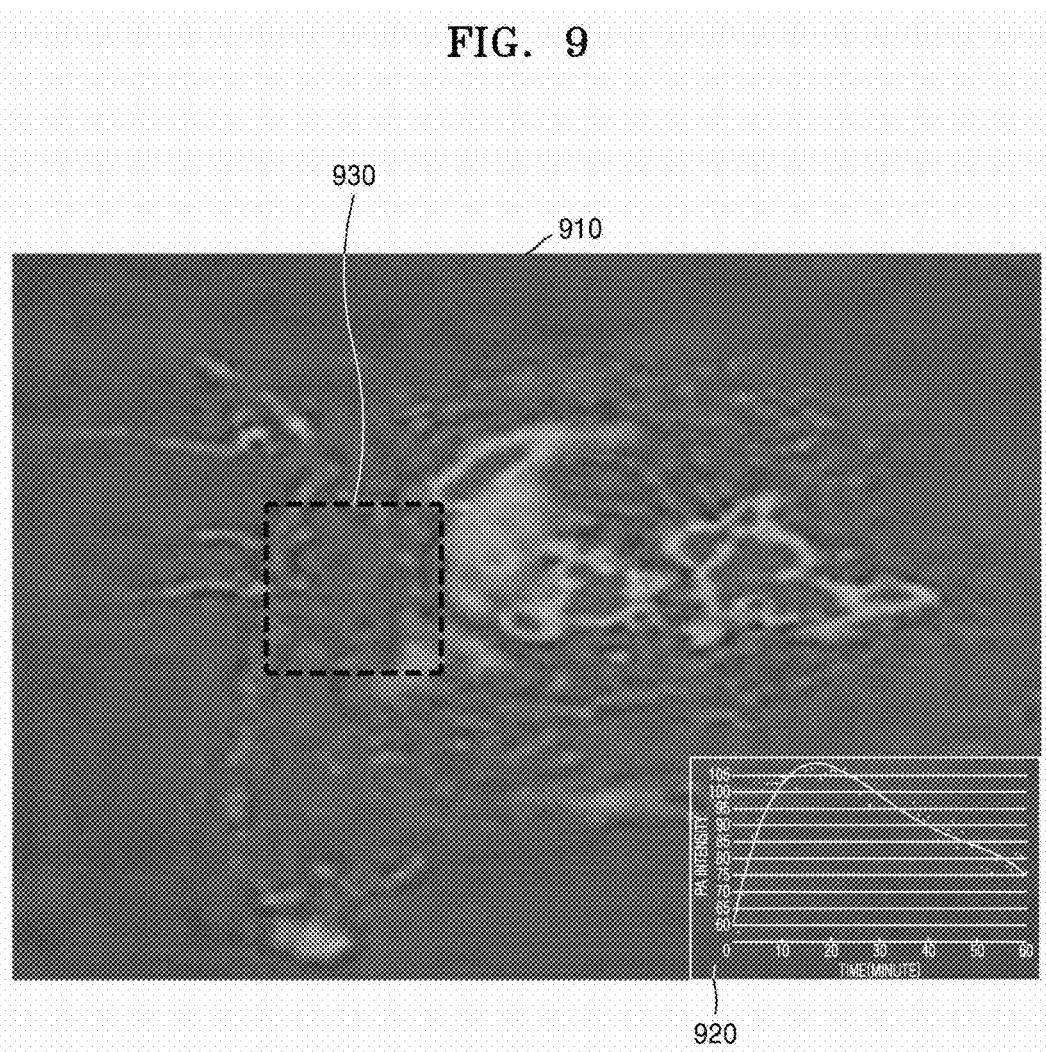
FIG. 9 is a diagram of a photoacoustic image and a TIC of a region of interest, according to an embodiment.

FIG. 8 is a flowchart illustrating a method of controlling a photoacoustic imaging diagnosis apparatus, according to an embodiment, and FIG. 9 is a diagram of a photoacoustic imaging diagnosis apparatus of a region of interest and a TIC, according to an embodiment.

According to the embodiment illustrated with reference to FIG. 8, the method of controlling a photoacoustic imaging diagnosis apparatus may include receiving an input for setting a region of interest 810, setting the region of interest on the photoacoustic image based on the setting input 820, receiving a photoacoustic signal from the region of interest 830, generating a TIC of the region of interest 840, and displaying the TIC of the region of interest 850.

In operation 810, the photoacoustic imaging diagnosis apparatus 300 may receive an input for setting a region of interest from outside.

According to an embodiment, the photoacoustic imaging diagnosis apparatus 300 may receive the input for setting the region of interest on the photoacoustic image. In addition, the photoacoustic imaging diagnosis apparatus 300 may receive an input for setting a region of interest that is at least one of the regions of the object 10. For example, as shown in FIG. 9, the photoacoustic imaging diagnosis apparatus 300 may receive an input for setting a region of interest 930 included in a photoacoustic image 910.

According to an embodiment, the region of interest may be set on an ultrasound image. For example, the region of interest may be set on an ultrasound image that is generated using an ultrasound echo signal transmitted from the object 10 before the administration of the contrast medium.

In operation 820, the photoacoustic imaging diagnosis apparatus 300 may set the region of interest on the photoacoustic image based on the input for setting the region of interest.

According to an embodiment, as shown in FIG. 9, the photoacoustic imaging diagnosis apparatus 300 may set a region of interest 930 by using the photoacoustic image 910.

According to an embodiment, the photoacoustic imaging diagnosis apparatus 300 may set a region of interest by using an ultrasound image.

In operation 830, the photoacoustic imaging diagnosis apparatus 300 may receive a photoacoustic signal from the set region of interest.

According to an embodiment, the photoacoustic imaging diagnosis apparatus 300 may receive a photoacoustic signal from the object 10 including the region of interest. The photoacoustic imaging diagnosis apparatus 300 may extract the photoacoustic signal regarding the region of interest from the photoacoustic signal transmitted from the object 10. The photoacoustic imaging diagnosis apparatus 300 may remove a photoacoustic signal that does not correspond to the region of interest, from the object 10.

In operation 840, the photoacoustic imaging diagnosis apparatus 300 may generate a TIC of the set region of interest.

According to an embodiment, the photoacoustic imaging diagnosis apparatus 300 may generate scan information of the region of interest by using the photoacoustic signal transmitted from the region of interest, and may generate the TIC of the region of interest by using the scan information.

According to an embodiment, the photoacoustic imaging diagnosis apparatus 300 may generate the TIC of the region of interest by using the photoacoustic signal regarding the region of interest, the photoacoustic signal being extracted from the photoacoustic signal transmitted from the object 10.

In operation 850, the photoacoustic imaging diagnosis apparatus 300 may display the generated TIC of the region of interest.

According to an embodiment, the photoacoustic imaging diagnosis apparatus 300 may display the set region of interest together with the TIC of the region of interest. For example, as shown in FIG. 9, a TIC 920 of the region of interest may be displayed with the region of interest 930 on the photoacoustic image 910.

According to an embodiment, the photoacoustic imaging diagnosis apparatus 300 may display the TIC of the region of interest with the ultrasound image of the object 10 and the region of interest set on the ultrasound image.

According to an embodiment, the photoacoustic imaging diagnosis apparatus 300 may display the TIC of the region of interest, with the photoacoustic image and the ultrasound image of the object 10, and the region of interest.

According to an embodiment, the photoacoustic imaging diagnosis apparatus 300 may display the region of interest in the object, the TIC of the region of interest, and an inclination of the TIC during a preset time period.

Figure 10:
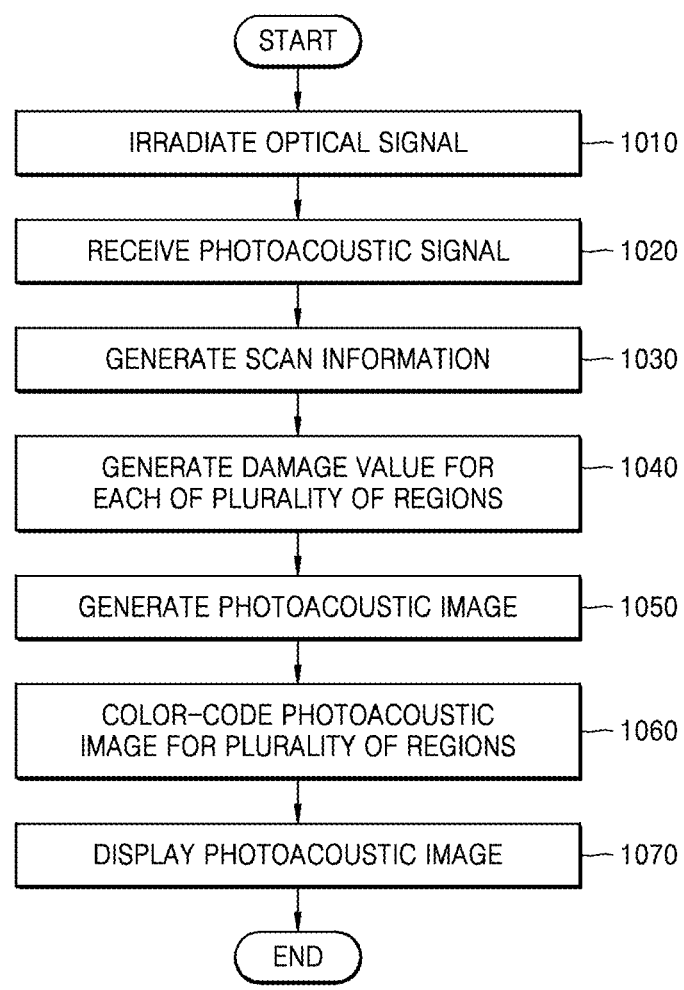
FIG. 10 is a flowchart illustrating a method of controlling a photoacoustic imaging diagnosis apparatus, according to an embodiment.
Figure 11:
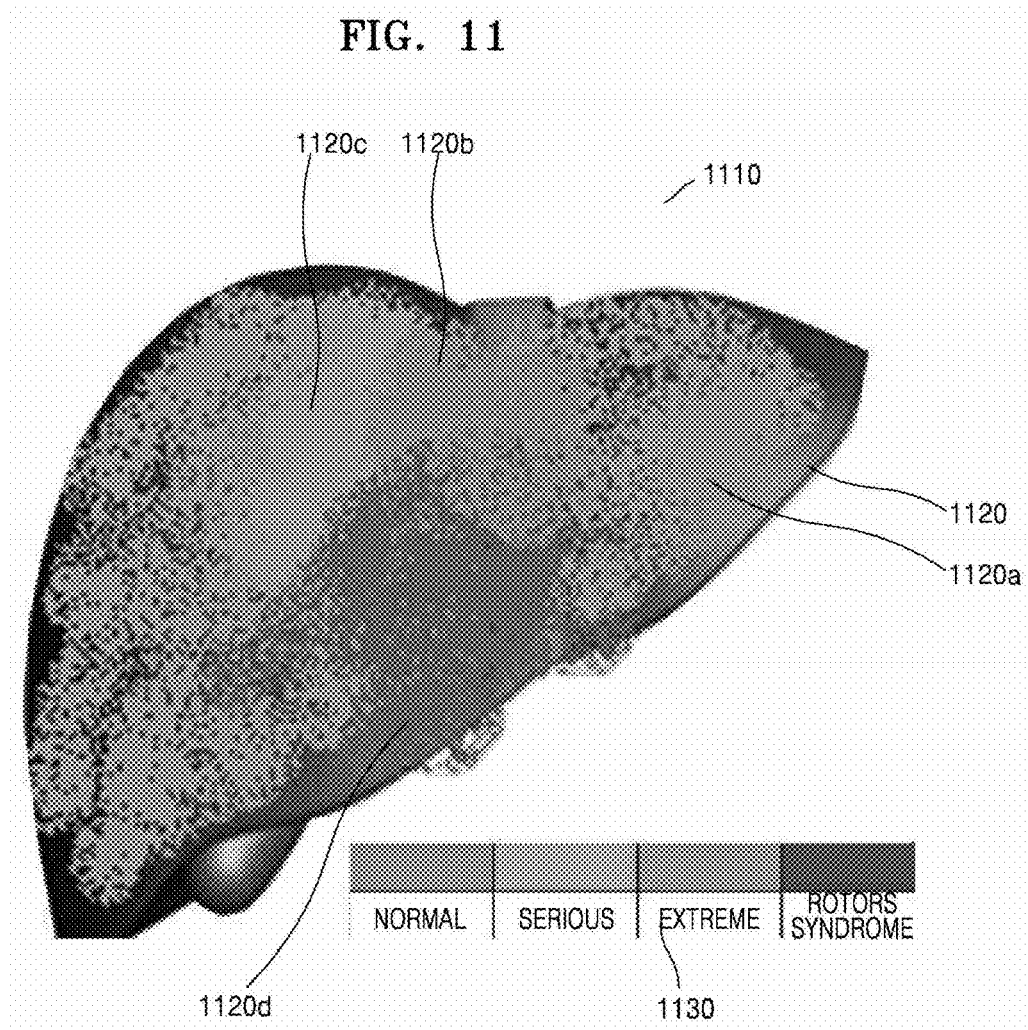
FIG. 11 is a diagram in which a plurality of regions in an object are represented in different colors according to damage degrees.

FIG. 10 is a flowchart illustrating a method of controlling a photoacoustic imaging diagnosis apparatus, according to an embodiment, and FIG. 11 is a diagram of a plurality of regions expressed in different colors according to damage degrees, in an object according to an embodiment.

According to the embodiment illustrated in FIG. 10, the method of controlling a photoacoustic imaging diagnosis apparatus may include irradiating an optical signal (1010), receiving a photoacoustic signal (1020), generating scan information (1030), generating a damage value with respect to each of a plurality of regions (1040), generating a photoacoustic image (1050), color-coding a photoacoustic image with respect to each of the plurality of regions (1060), and displaying the photoacoustic image (1070).

In operation 1010, the photoacoustic imaging diagnosis apparatus 300 may irradiate the optical signal to the object 10. The photoacoustic imaging diagnosis apparatus 300 may irradiate the optical signal to the plurality of regions of the object 10.

Since operation 1010 is similar to operation 410 and operation 510, detailed descriptions thereof are omitted.

In operation 1020, the photoacoustic imaging diagnosis apparatus 300 may receive a photoacoustic signal generated by the object 10. The photoacoustic imaging diagnosis apparatus 300 may receive photoacoustic signals from the plurality of regions of the object 10. Since operation 1020 is similar to operation 420 and operation 520, detailed descriptions thereof are omitted.

In operation 1030, the photoacoustic imaging diagnosis apparatus 300 may generate scan information representing the intensity of the received photoacoustic signal by using the photoacoustic signal. The photoacoustic imaging diagnosis apparatus 300 may generate scan information with respect to each of the plurality of regions of the object 10. Since operation 1030 is similar to operation 430 and operation 530, detailed descriptions thereof are omitted.

In operation 1040, the photoacoustic imaging diagnosis apparatus 300 may generate a damage value by digitizing a damage degree of the object 10. The photoacoustic imaging diagnosis apparatus 300 may generate the damage value of each of the plurality of regions, by using the scan information of each of the plurality of regions of the object 10.

In operation 1050, the photoacoustic imaging diagnosis apparatus 300 may generate a photoacoustic image by using the photoacoustic signal. The photoacoustic imaging diagnosis apparatus 300 may generate photoacoustic data, by performing analog/digital conversion on the photoacoustic signal, and combining the signals that are digitally converted by taking into account locations of a plurality of transducers and focusing points. The photoacoustic imaging diagnosis apparatus 300 may generate the photoacoustic image by converting the photoacoustic data into the photoacoustic image.

In operation 1060, the photoacoustic imaging diagnosis apparatus 300 may perform color-coding on the photoacoustic image with respect to each of the plurality of regions of the object 10.

According to an embodiment, the photoacoustic imaging diagnosis apparatus 300 may perform color-coding on the plurality of regions of the photoacoustic image in colors respectively corresponding to the damage values of the plurality of regions.

According to an embodiment, the photoacoustic imaging diagnosis apparatus 300 may determine a color corresponding to the damage value of each of the plurality of regions, by comparing the damage value with a preset value. For example, the photoacoustic imaging diagnosis apparatus 300 may determine a state of a region, in which a ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is less than 10%, as a normal state, and may determine a first color (e.g., green) as a color corresponding to the normal state.

The photoacoustic imaging diagnosis apparatus 300 may determine a state of a region, in which a ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is between 10% to 20%, as a cautious state, and determine a second color (e.g., blue) as a color corresponding to the cautious state.

The photoacoustic imaging diagnosis apparatus 300 may determine a state of a region, in which a ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is between 20% to 30%, as a serious state, and determine a third color (e.g., yellow) as a color corresponding to the serious state.

For example, the photoacoustic imaging diagnosis apparatus 300 may determine a state of a region, in which a ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is greater than 30% and less than 40%, as an extreme state, and may determine a fourth color (e.g., orange) as a color corresponding to the extreme state.

The photoacoustic imaging diagnosis apparatus 300 may determine a state of a region, in which a ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is equal to or greater than 40%, as a rotors syndrome state, and determine a fifth color (e.g., red) as a color corresponding to the rotors syndrome state. However, one or more embodiments are not limited to the above examples.

According to an embodiment, as shown in FIG. 11, the photoacoustic imaging diagnosis apparatus 300 may color-code the photoacoustic image according to a damage degree of each of a plurality of regions of a liver 1120. For example, the photoacoustic imaging diagnosis apparatus 300 may color-code a region 1120a in the normal state as green, a region 1120c in the serious state as yellow, a region 1120b in the extreme state as orange, and a region 1120d in the rotors syndrome state as red. However, one or more embodiments are not limited to the above examples.

In operation 1070, the photoacoustic imaging diagnosis apparatus 300 may display the photoacoustic image.

According to an embodiment, the photoacoustic imaging diagnosis apparatus 300 may display the color-coded photoacoustic image. For example, as shown in FIG. 11, the photoacoustic imaging diagnosis apparatus 300 may display the color-coded photoacoustic image according to the damage degrees of the plurality of regions of the liver 1120. The display 350 may display the photoacoustic image, in which the region 1120a in the normal state is color-coded as green, the region 1120c in the serious state is color-coded as yellow, the region 1120b in the extreme state is color-coded as orange, and the region 1120d in the rotors syndrome state is color-coded as red, but is not limited thereto.

According to an embodiment, the photoacoustic imaging diagnosis apparatus 300 may display the color-coded photoacoustic image, together with a color reference table 1130.

According to an embodiment, the photoacoustic imaging diagnosis apparatus 300 may display the color-coded photoacoustic image, together with the ultrasound image and at least one of the TICs of the plurality of regions.

Figure 12:
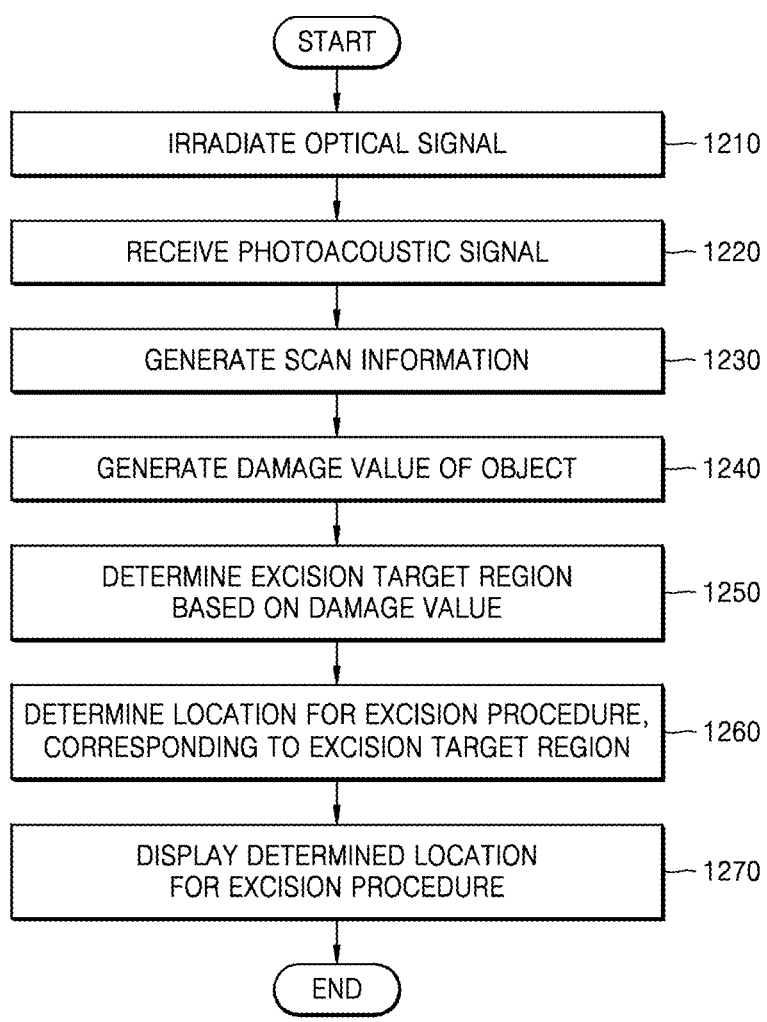
FIG. 12 is a flowchart illustrating a method of controlling a photoacoustic imaging diagnosis apparatus, according to an embodiment.

FIG. 12 is a flowchart illustrating a method of controlling a photoacoustic imaging diagnosis apparatus, according to an embodiment.

According to the embodiment illustrated with reference to FIG. 12, the method of controlling a photoacoustic imaging diagnosis apparatus may include irradiating an optical signal 1210, receiving a photoacoustic signal 1220, generating scan information 1230, generating a damage value of an object 1240, determining an excision target region by using the damage value 1250, determining an excision procedure location corresponding to the determined excision target region 1260, and displaying the determined excision procedure location 1270.

Since operation 1210 is similar to operation 410, operation 510, and operation 1010, detailed descriptions thereof are omitted.

Since operation 1220 is similar to operation 420, operation 520, and operation 1020, detailed descriptions thereof are omitted.

Since operation 1230 is similar to operation 430, operation 530, and operation 1030, detailed descriptions thereof are omitted.

Operation 1240 is similar to operation 1040, and detailed descriptions thereof are omitted.

In operation 1250, the photoacoustic imaging diagnosis apparatus 300 may determine an excision target region by using the generated damage value.

According to an embodiment, the photoacoustic imaging diagnosis apparatus 300 may determine the excision target region by comparing the generated damage value with a predetermined value. For example, the photoacoustic imaging diagnosis apparatus 300 may compare an average value of the intensity versus time of the photoacoustic signal transmitted from the object 10, with a preset value. The photoacoustic imaging diagnosis apparatus 300 may determine the excision target region based on a preset excision target region corresponding to a preset value.

According to an embodiment, the photoacoustic imaging diagnosis apparatus 300 may determine the excision target region by comparing the damage value of each of the plurality of regions with the preset value. For example, the photoacoustic imaging diagnosis apparatus 300 may determine the excision target region based on a location of the region, a location where a lesion occurs, and a damage value on the region.

According to an embodiment, the photoacoustic imaging diagnosis apparatus 300 may compare a ratio between an intensity of the photoacoustic signal received by the photoacoustic imaging diagnosis apparatus 300 at the time of administering the ICG from each of a plurality of regions in the liver and an intensity of the photoacoustic signal received by the photoacoustic imaging diagnosis apparatus 300 at 15 minutes after the time of administering the ICG, with the preset value. According to a result of the comparison, the photoacoustic imaging diagnosis apparatus 300 may determine the excision target region based on the damage value of each of the plurality of regions, a location of the region with severe damage, and a location where the lesion occurs.

In operation 1260, the photoacoustic imaging diagnosis apparatus 300 may determine the excision procedure location corresponding to the determined excision target region.

According to an embodiment, the photoacoustic imaging diagnosis apparatus 300 may determine the location for the excision procedure, along with an outskirt of the determined excision target region.

According to an embodiment, the photoacoustic imaging diagnosis apparatus 300 may determine the location and order of the excision procedure, according to the location of the excision target region.

In operation 1270, the photoacoustic imaging diagnosis apparatus 300 may display the determined location for the excision procedure.

According to an embodiment, the photoacoustic imaging diagnosis apparatus 300 may display the determined location for the excision procedure, together with at least one of the photoacoustic image and the ultrasound image.

According to an embodiment, the photoacoustic imaging diagnosis apparatus 300 may display the excision target region and the location for the excision procedure on the photoacoustic image of the object 10. For example, the photoacoustic imaging diagnosis apparatus 300 may express the location for the excision procedure with a line. The photoacoustic imaging diagnosis apparatus 300 may express the location for the excision procedure with a line of a color that is not used in the photoacoustic image. The photoacoustic imaging diagnosis apparatus 300 may represent the excision target region in a different color from the other regions, so that the location for the excision procedure may be expressed along the outskirt of the excision target region.

According to an embodiment, the photoacoustic imaging diagnosis apparatus 300 may display the excision target region and the location for the excision procedure on the ultrasound image of the object 10.

According to an embodiment, the photoacoustic imaging diagnosis apparatus 300 may display the photoacoustic image and the ultrasound image of the object 10 to overlap with each other, and then, may display the excision target region and the location for the excision procedure.

The photoacoustic imaging diagnosis apparatus 300 may indicate the location of the excision procedure corresponding to the damage degree of the object 10 in the noninvasive manner. For example, the photoacoustic imaging diagnosis apparatus 300 may indicate the location for the excision procedure corresponding to a damage degree of the liver, by determining the liver reserve function. The photoacoustic imaging diagnosis apparatus 300 may indicate the location for the excision procedure corresponding to the damage degree of the liver of a patient who needs to get a hepatic resection. The photoacoustic imaging diagnosis apparatus 300 may determine a damage degree of the liver of a living donor, and then, may indicate whether to possibly excise the liver and the location for the excision procedure.

Figure 13:
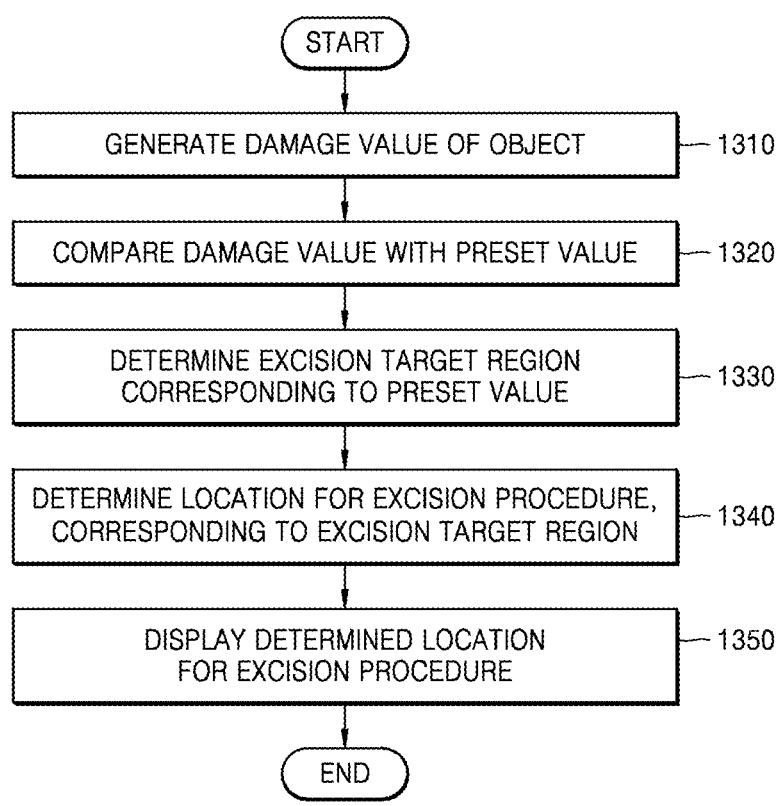
FIG. 13 is a flowchart illustrating a method of controlling a photoacoustic imaging diagnosis apparatus, according to an embodiment.
Figure 14A:
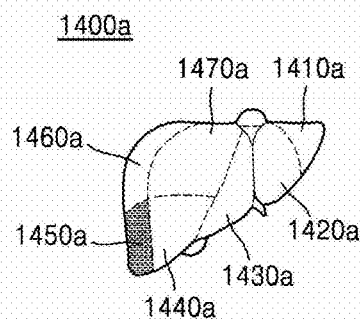
FIGS. 14A to 14C are diagrams showing a location for an excision procedure according to an embodiment.
Figure 14B:
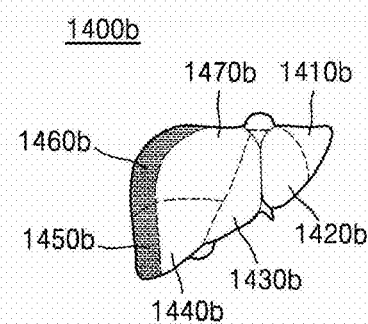
Figure 14C:
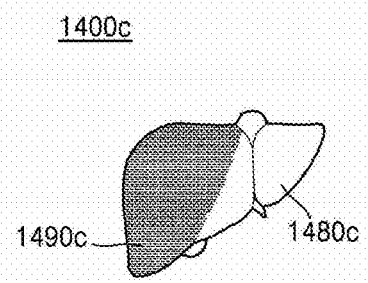

FIG. 13 is a flowchart illustrating a method of controlling a photoacoustic imaging diagnosis apparatus, according to an embodiment, and FIGS. 14A to 14C are diagrams showing a location for an excision procedure according to an embodiment.

According to the embodiment illustrated with reference to FIG. 13, the method of controlling a photoacoustic imaging diagnosis apparatus may include generating a damage value of an object 1310, comparing the damage value with a preset value 1320, determining an excision target region corresponding to the preset value 1330, determining a location for an excision procedure, the location corresponding to the excision target region 1340, and displaying the determined location for the excision procedure 1350.

In operation 1310, the photoacoustic imaging diagnosis apparatus 300 may generate the damage value of the object 10 based on scan information.

According to an embodiment, the photoacoustic imaging diagnosis apparatus 300 may generate a damage value of the object 10 by using an average value of the intensity of the photoacoustic signal transmitted from the object 10.

According to an embodiment, the photoacoustic imaging diagnosis apparatus 300 may generate a damage value of the object 10 by using an average value of the intensity of the photoacoustic signal transmitted from each of the plurality of regions of the object 10.

According to an embodiment, the photoacoustic imaging diagnosis apparatus 300 may generate a damage value of the object 10 by using an average value of the intensity of the photoacoustic signal transmitted from each of the plurality of regions of the object 10, at a time point right after the administration of the ICG and 15 minutes after the administration of the ICG.

In operation 1320, the photoacoustic imaging diagnosis apparatus 300 may compare the generated damage value with a preset value.

According to an embodiment, the photoacoustic imaging diagnosis apparatus 300 may compare a damage value of the object 10 generated using an average value of the intensity of the photoacoustic signal transmitted from each of the plurality of regions of the object 10, with a preset value.

According to an embodiment, the photoacoustic imaging diagnosis apparatus 300 may compare a damage value of the object 10 with a preset value, wherein the damage value is generated using an average value of the intensity of the photoacoustic signal transmitted from each of the plurality of regions of the object 10, at a time point right after the administration of the ICG and 15 minutes after the administration of the ICG.

In operation 1330, the photoacoustic imaging diagnosis apparatus 300 may determine an excision target region corresponding to the preset value.

According to an embodiment, the photoacoustic imaging diagnosis apparatus 300 may determine the excision target region corresponding to the preset value that is compared with the average value of the intensity of the photoacoustic signal transmitted from the object 10.

According to an embodiment, the photoacoustic imaging diagnosis apparatus 300 may determine the excision target region corresponding to the preset value that is compared with a ratio between the intensity of the photoacoustic signal at the time point of administering the ICG and the intensity of the photoacoustic signal at 15 minutes after the administration of the ICG.

According to an embodiment, as shown in FIG. 14A, the photoacoustic imaging diagnosis apparatus 300 may classify a liver 1400a into a plurality of regions 1410a, 1420a, 1430a, 1440a, 1450a, 1460a, and 1470a, and may determine at least one of the plurality of regions 1410a, 1420a, 1430a, 1440a, 1450a, 1460a, and 1470a as the excision target region.

According to an embodiment, as shown in FIG. 14B, the photoacoustic imaging diagnosis apparatus 300 may classify a liver 1400b into a plurality of regions 1410b, 1420b, 1430b, 1440b, 1450b, 1460b, and 1470b, and may determine a combined region of adjacent regions 1450b and 1460b among the plurality of regions 1410b, 1420b, 1430b, 1440b, 1450b, 1460b, and 1470b as the excision target region.

According to an embodiment, as shown in FIG. 14C, the photoacoustic imaging diagnosis apparatus 300 may determine a left lobe 1480c or a right lobe 1490c of a liver 1400c as the excision target region.

According to an embodiment, in a case where the ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is less than 10%, the photoacoustic imaging diagnosis apparatus 300 may determine some of the plurality of regions of the liver as the excision target region. For example, as shown in FIG. 14A, the photoacoustic imaging diagnosis apparatus 300 may classify a liver 1400a into a plurality of regions 1410a, 1420a, 1430a, 1440a, 1450a, 1460a, and 1470a, and may determine at least one of the plurality of regions 1410a, 1420a, 1430a, 1440a, 1450a, 1460a, and 1470a as the excision target region. In addition, as shown in FIG. 14B, the photoacoustic imaging diagnosis apparatus 300 may classify a liver 1400b into a plurality of regions 1410b, 1420b, 1430b, 1440b, 1450b, 1460b, and 1470b, and may determine a combined region of adjacent regions 1450b and 1460b among the plurality of regions 1410b, 1420b, 1430b, 1440b, 1450b, 1460b, and 1470b as the excision target region. In addition, as shown in FIG. 14C, the photoacoustic imaging diagnosis apparatus 300 may determine a left lobe 1480c or a right lobe 1490c of a liver 1400c as the excision target region.

According to an embodiment, in a case where the ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is equal to or greater than 10% and less than 20%, the photoacoustic imaging diagnosis apparatus 300 may determine some of the plurality of regions of the liver as the excision target region. For example, as shown in FIG. 14A, the photoacoustic imaging diagnosis apparatus 300 may classify a liver 1400a into a plurality of regions 1410a, 1420a, 1430a, 1440a, 1450a, 1460a, and 1470a, and may determine at least one of the plurality of regions 1410a, 1420a, 1430a, 1440a, 1450a, 1460a, and 1470a as the excision target region. In addition, as shown in FIG. 14B, the photoacoustic imaging diagnosis apparatus 300 may classify a liver 1400b into a plurality of regions 1410b, 1420b, 1430b, 1440b, 1450b, 1460b, and 1470b, and may determine a combined region of adjacent regions 1450b and 1460b among the plurality of regions 1410b, 1420b, 1430b, 1440b, 1450b, 1460b, and 1470b as the excision target region. In addition, as shown in FIG. 14C, the photoacoustic imaging diagnosis apparatus 300 may determine a left lobe 1480c or a right lobe 1490c of a liver 1400c as the excision target region.

According to an embodiment, in a case where the ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is equal to or greater than 20% and less than 30%, the photoacoustic imaging diagnosis apparatus 300 may determine some of the plurality of regions of the liver as the excision target region. For example, as shown in FIG. 14B, the photoacoustic imaging diagnosis apparatus 300 may classify a liver 1400b into a plurality of regions 1410b, 1420b, 1430b, 1440b, 1450b, 1460b, and 1470b, and may determine a combined region of adjacent regions 1450b and 1460b among the plurality of regions 1410b, 1420b, 1430b, 1440b, 1450b, 1460b, and 1470b as the excision target region. In addition, as shown in FIG. 14C, the photoacoustic imaging diagnosis apparatus 300 may determine a left lobe 1480c or a right lobe 1490c of a liver 1400c as the excision target region.

According to an embodiment, in a case where the ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is equal to or greater than 30% and less than 40%, the photoacoustic imaging diagnosis apparatus 300 may determine some of the plurality of regions of the liver as the excision target region. For example, as shown in FIG. 14C, the photoacoustic imaging diagnosis apparatus 300 may determine a left lobe 1480c or a right lobe 1490c of a liver 1400c as the excision target region.

According to an embodiment, in a case where the ratio between an intensity of the photoacoustic signal received by the photoacoustic imaging diagnosis apparatus 300 at a time point of administering the ICG and an intensity of the photoacoustic signal received by the photoacoustic imaging diagnosis apparatus 300 after 15 minutes from the administration of the ICG is equal to or greater than 40%, the photoacoustic imaging diagnosis apparatus 300 may determine the entire liver as the excision target region or may determine the excision procedure to be impossible and may not determine the excision target region.

Operation 1340 is similar to operation 1260, and detailed descriptions thereof are omitted.

Operation 1350 is similar to operation 1270, and detailed descriptions thereof are omitted.

Figure 15:
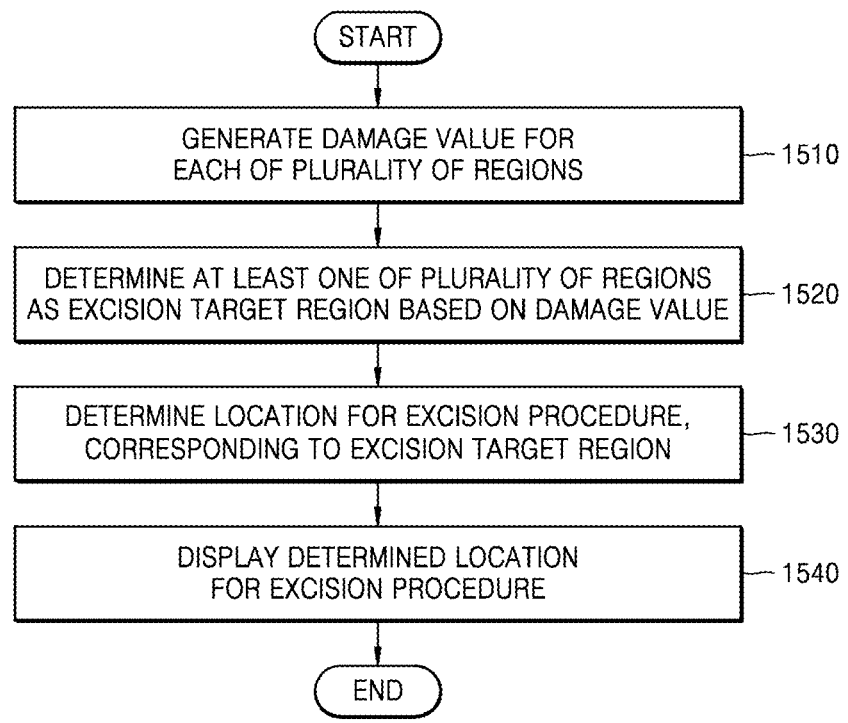
FIG. 15 is a flowchart illustrating a method of controlling a photoacoustic imaging diagnosis apparatus, according to an embodiment.
Figure 16:
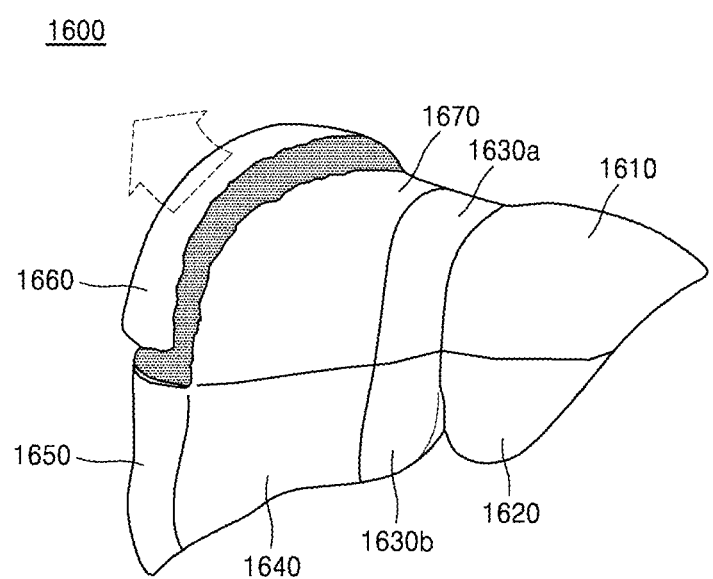
FIG. 16 is a diagram of a location for an excision procedure according to an embodiment.

FIG. 15 is a flowchart illustrating a method of controlling a photoacoustic imaging diagnosis apparatus, according to an embodiment, and FIG. 16 is a diagram showing a location of an excision procedure according to an embodiment.

According to the embodiment illustrated with reference to FIG. 15, the method of controlling a photoacoustic imaging diagnosis apparatus may include generating a damage value for each of the plurality of regions 1510, determining at least one of the plurality of regions as an excision target region by using the damage value 1520, determining a location for an excision procedure corresponding to the excision target region 1530, and displaying the determined location for the excision procedure 1540.

In operation 1510, the photoacoustic imaging diagnosis apparatus 300 may generate a damage value for each of the plurality of regions of the object 10.

According to an embodiment, as shown in FIG. 16, the photoacoustic imaging diagnosis apparatus 300 may generate a damage value for each of a plurality of regions 1610, 1620, 1630a, 1630b, 1640, 1650, 1660, and 1670 of a liver 1600.

According to an embodiment, the photoacoustic imaging diagnosis apparatus 300 may generate a damage value for each of the plurality of regions 1610, 1620, 1630a, 1630b, 1640, 1650, 1660, and 1670 of the liver 1600 both at a time point of administering the ICG and at 15 minutes after the administration of the ICG.

In operation 1520, the photoacoustic imaging diagnosis apparatus 300 may determine at least one of the plurality of regions 1610, 1620, 1630a, 1630b, 1640, 1650, 1660, and 1670 as an excision target region by using the generated damage values.

According to an embodiment, as shown in FIG. 16, the photoacoustic imaging diagnosis apparatus 300 may determine at least one 1660 of the plurality of regions 1610, 1620, 1630a, 1630b, 1640, 1650, 1660, and 1670 as an excision target region by using the damage value of each of the plurality of regions 1610, 1620, 1630a, 1630b, 1640, 1650, 1660, and 1670 of the liver 1600.

According to an embodiment, the photoacoustic imaging diagnosis apparatus 300 may determine at least one of the plurality of regions as the excision target region by using the damage value of each of the plurality of regions, a location of the lesion, and the location of each region. For example, if the lesion is located in one of the plurality of regions, for example, the region 1660, and the damage value of the region 1660 is equal to or greater than the preset value, the photoacoustic imaging diagnosis apparatus 300 may determine the region 1660 as the excision target region.

Since operation 1530 is similar to operation 1260 and operation 1340, detailed descriptions thereof are omitted.

Since operation 1540 is similar to operation 1270 and operation 1350, detailed descriptions thereof are omitted.

Figure 17A:
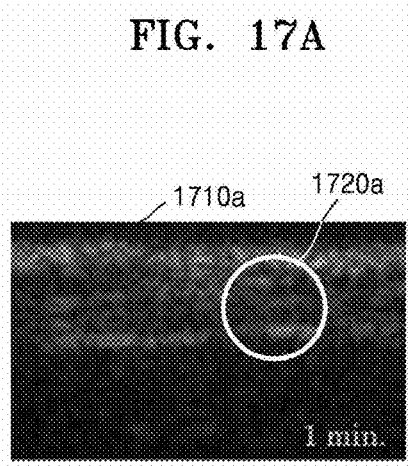
FIGS. 17A to 17D are diagrams of a photoacoustic image and FIG. 17E is a TIC with respect to a control group, according to an embodiment.
Figure 17B:
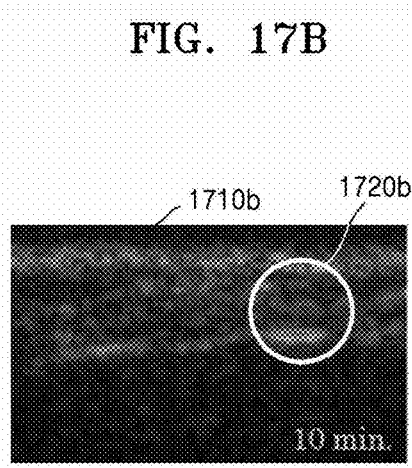
Figure 17C:
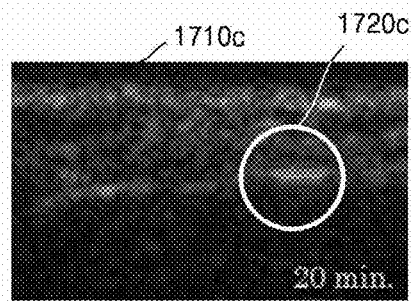
Figure 17D:
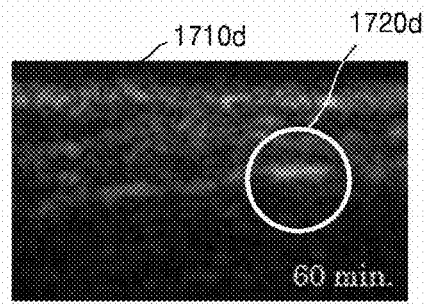
Figure 17E:
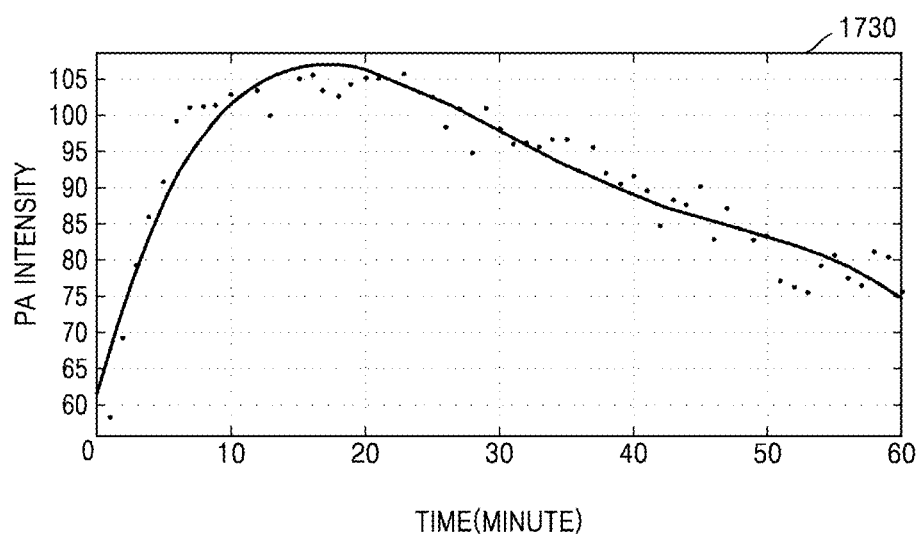
Figure 18A:
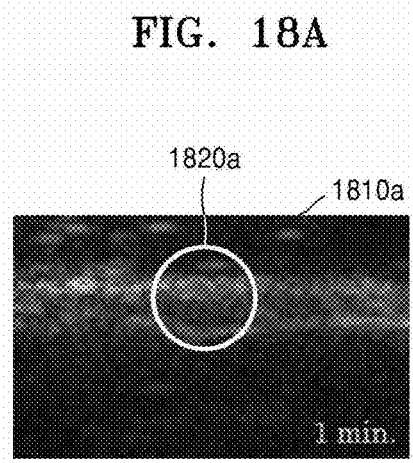
FIGS. 18A to 18D are diagrams of a photoacoustic image and FIG. 18E a TIC with respect to an experimental group, according to an embodiment.
Figure 18B:
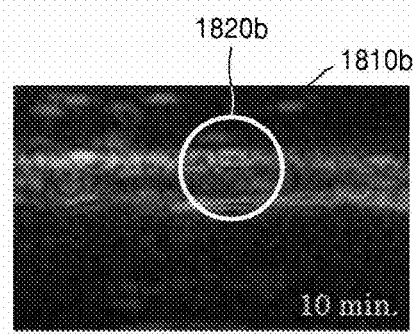
Figure 18C:
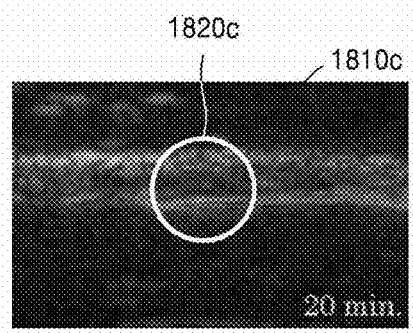
Figure 18D:
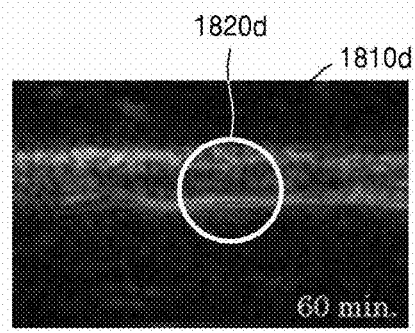
Figure 18E:
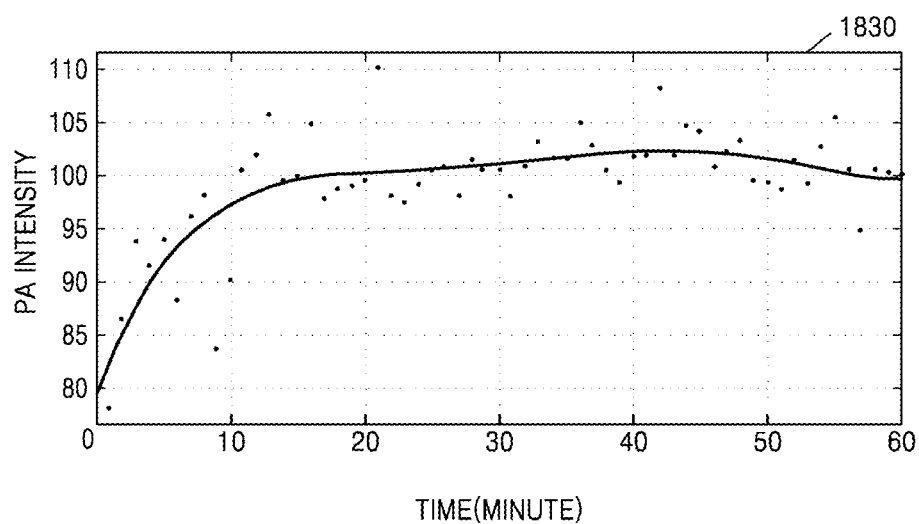

FIGS. 17A to 17D are diagrams of a photoacoustic image and FIG. 17E is a TIC with respect to a control group, according to an embodiment, and FIGS. 18A to 18D are diagrams of a photoacoustic image and FIG. 18E a TIC with respect to an experimental group, according to an embodiment.

FIGS. 17A to 17D are photoacoustic images of a laboratory rat having a normal liver to which ICG is injected at a preset time point, and FIG. 17E is a graph illustrating a TIC of the laboratory rat having a normal liver to which the ICG is injected.

A photoacoustic image 1710a is generated using a photoacoustic signal transmitted from the laboratory rat after 1 minute from the time point of administering the ICG, a photoacoustic image 1710b is generated using a photoacoustic signal transmitted from the laboratory rat after 10 minutes from the administration of the ICG, a photoacoustic image 1710c is generated using a photoacoustic signal transmitted from the laboratory rat after 20 minutes from the administration of the ICG, and a photoacoustic image 1710d is generated using a photoacoustic signal transmitted from the laboratory rat after 60 minutes from the administration of the ICG.

A region 1720a is a region of the liver of the laboratory rat, in a photoacoustic signal after 1 minute from the time point of administering the ICG, a region 1720b is a region of the liver of the laboratory rat, in a photoacoustic signal after 10 minutes from the administration of the ICG, and a region 1720c is a region of the liver of the laboratory rat, in a photoacoustic signal after 20 minutes from the administration of the ICG, and a region 1720d is a region of the liver of the laboratory rat, in a photoacoustic signal after 60 minutes from the administration of the ICG.

A graph 1730 shows a TIC generated using photoacoustic signals transmitted from the liver of the laboratory rat for 1 hour after the administration of the ICG.

Referring to 1720a to 1720d, and 1730, the photoacoustic signal transmitted from the liver of the laboratory rat is detected to have the greatest intensity at 10 minutes to 20 minutes after the administration of the ICG, and the liver is expressed red in the photoacoustic image. When the time after the administration of the ICG exceeds 20 minutes, the ICG is removed over time and the red region is gradually switched to blue in the photoacoustic image.

That is, the laboratory rat having a normal liver detoxifies the ICG in the liver and removes the ICG with the gallbladder, and thus, as time passes, the photoacoustic intensity decreases on the TIC.

FIGS. 18A to 18D are photoacoustic images of a laboratory rat having a liver, in which acute hepatitis is caused by D-galactosamine including ICG, and FIG. 18E is a TIC of the laboratory rat having a liver, in which acute hepatitis is caused by D-galactosamine including the ICG (GOT or GPT is 400 IU or greater).

A photoacoustic image 1810a is generated using a photoacoustic signal transmitted from the laboratory rat after 1 minute from the time point of administering the ICG, a photoacoustic image 1810b is generated using a photoacoustic signal transmitted from the laboratory rat after 10 minutes from the administration of the ICG, a photoacoustic image 1810c is generated using a photoacoustic signal transmitted from the laboratory rat after 20 minutes from the administration of the ICG, and a photoacoustic image 1810d is generated using a photoacoustic signal transmitted from the laboratory rat after 60 minutes from the administration of the ICG.

A region 1820a is a region of the liver of the laboratory rat, in a photoacoustic signal after 1 minute from the time point of administering the ICG, a region 1820b is a region of the liver of the laboratory rat, in a photoacoustic signal after 10 minutes from the administration of the ICG, and a region 1820c is a region of the liver of the laboratory rat, in a photoacoustic signal after 20 minutes from the administration of the ICG, and a region 1820d is a region of the liver of the laboratory rat, in a photoacoustic signal after 60 minutes from the administration of the ICG.

A graph 1830 shows a TIC generated using photoacoustic signals transmitted from the liver of the laboratory rat for 1 hour after the administration of the ICG.

Referring to 1820a to 1820d, and 1830, the photoacoustic image of the liver of the laboratory rat is expressed red even after 10 minutes has passed from the administration of the ICG. The intensity of the photoacoustic signal from the laboratory rat does not decrease over time, but is maintained at a constant level on the TIC 1830. The laboratory rat having a liver with hepatitis is not able to detoxify the ICG in the liver. The damaged state of the liver may be determined based on the TIC generated using the intensity of the photoacoustic signal.

When an inclination between 20 minutes to 30 minutes on the TIC of the graph 1730 is compared with an inclination between 20 minutes to 30 minutes on the TIC of the graph 1830, the inclination between 20 minutes to 30 minutes on the TIC of the graph 1730 is greater than the inclination between 20 minutes to 30 minutes on the TIC of the graph 1830.

When an inclination between 20 minutes to 60 minutes on the TIC of the graph 1730 is compared with an inclination between 20 minutes to 60 minutes on the TIC of the graph 1830, the inclination between 20 minutes to 60 minutes on the TIC of the graph 1730 is greater than the inclination between 20 minutes to 60 minutes on the TIC of the graph 1830.

That is, the TIC generated based on the intensity of the photoacoustic signal from the laboratory rat having a normal liver has a greater inclination than that of the TIC generated based on the intensity of the photoacoustic signal from the laboratory rat having a liver with hepatitis. Therefore, the damaged state of the liver may be determined based on the inclination of the TIC that is generated based on the intensity of the photoacoustic signal during a preset time period. The damaged state of the liver may be determined based on the variation in the intensity of the photoacoustic signal during the preset time period.

The embodiments provided herein may be implemented as a computer-readable recording medium for storing computer-executable commands and data. The above commands may be stored as program code, and when being executed by a processor, a predetermined program module may be generated to perform a predetermined operation. Also, the above commands, when being executed by the processor, may perform predetermined operations of the embodiments provided herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of controlling a photoacoustic imaging diagnosis apparatus, the method comprising:
    irradiating, to a liver of an object, an optical signal having a wavelength corresponding to an optical energy absorption wavelength of a contrast medium that is injected to the object
    receiving a photoacoustic signal generated from the liver in response to the optical signal;
    generating scan information representing an intensity of the photoacoustic signal based on the photoacoustic signal;
    determining a damage degree of the liver based on an amount by which the intensity of the photoacoustic signal is reduced during a predetermined time using the scan information;
    identifying an excision target region of the liver from among a plurality of regions classified according to the damage degree;
    determining a location for an excision procedure corresponding to the excision target region; and
    displaying the damage degree of the liver and the location for the excision procedure of the liver,
    wherein the determining of the damage degree of the liver comprises determining a reserve function of the liver based on a ratio between a first intensity of the photoacoustic signal at a first time point of administering the contrast medium and a second intensity of the photoacoustic signal at a second time point that is the predetermined time after the first time point, and
    wherein the determining the location for the excision procedure comprises determining the location of the excision procedure corresponding to the reserve function of the liver.

2. The method of claim 1, wherein the scan information comprises information about the intensity of the photoacoustic signal with respect to each of a plurality of regions of the liver,
    the determining of the damage degree of the liver comprises generating a respective damage value of each of the plurality of regions by digitizing a respective damage degree in each of the plurality of regions, and
    the displaying of the damage degree of the liver and the location for the excision procedure of the liver further comprises:
        generating a photoacoustic image corresponding to the liver by using the photoacoustic signal;
        color-coding the photoacoustic image in colors corresponding to the respective damage values of the plurality of regions; and
        displaying the color-coded photoacoustic image.

3. A non-transitory computer-readable recording medium having embodied thereon a program for executing the method of controlling the photoacoustic imaging diagnosis apparatus according to claim 1.

4. The method of claim 1, wherein the displaying of the damage degree of the liver and the location for the excision procedure of the liver further comprises:
    generating a photoacoustic image by using the photoacoustic signal and a time intensity curve (TIC) representing a variation in the intensity of the photoacoustic signal according to time, based on the scan information; and
    displaying the TIC and the photoacoustic image.

5. The method of claim 4, further comprising:
    receiving an input for setting a region of interest; and
    setting the region of interest in the photoacoustic image, based on the input,
    wherein the scan information comprises information representing the intensity of the photoacoustic signal transmitted from the region of interest, and the TIC is about the photoacoustic signal transmitted from the region of interest.

6. The method of claim 1, wherein the identifying of the excision target region of the liver comprises:
    generating a damage value by digitizing the damage degree of the liver; and
    identifying the excision target region of the liver according to the damage value.

7. The method of claim 6, further comprising
    storing excision target regions corresponding to preset values, and
    the identifying of the excision target region of the liver comprises identifying the excision target region corresponding to the damage value by comparing the damage value with the preset values.

8. The method of claim 6, wherein the scan information comprises information about the intensity of the photoacoustic signal with respect to each of a plurality of regions of the liver,
    the generating of the damage value comprises generating a damage value for each of the plurality of regions by digitizing a damage degree in each of the plurality of regions, and
    the determining of the excision target region of the liver comprises determining at least one of the plurality of regions as the excision target region by using the damage value of each of the plurality of regions.

9. A photoacoustic imaging diagnosis apparatus comprising:
    an optical signal transmitter configured to irradiate, to a liver of an object, an optical signal having a wavelength corresponding to an optical energy absorption wavelength of a contrast medium that is injected to the object;
    an ultrasound probe configured to receive a photoacoustic signal generated from the liver in response to the optical signal;
    at least one processor configured to generate scan information representing an intensity of the photoacoustic signal based on the photoacoustic signal, determine a damage degree of the liver based on an amount by which the intensity of the photoacoustic signal is reduced during a predetermined time using the scan information, identify an excision target region of the liver from among a plurality of regions classified according to the damage degree, and determine a location for an excision procedure corresponding to the excision target region; and
    a display configured to display the damage degree of the liver and the location for the excision procedure of the liver, wherein the at least one processor is configured to,
determine a reserve function of the liver based on a ratio between a first intensity of the photoacoustic signal at a first time point of administering the contrast medium and a second intensity of the photoacoustic signal at a second time point that is a predetermined time after the first time point, and
identify the excision target region of the liver from among a plurality of regions classified according to the damage degree, and determine the location for the excision procedure corresponding to the excision target region based on the reserve function of the liver,
wherein the display is configured to display the location for the excision procedure of the liver.

10. The photoacoustic imaging diagnosis apparatus of claim 9, wherein the at least one processor generates the scan information comprising information about the intensity of a photoacoustic signal with respect to each of a plurality of regions of the liver, generates a respective damage value for each of the plurality of regions by digitizing a respective damage degree in each of the plurality of regions based on the scan information, generates a photoacoustic image corresponding to the liver by using the photoacoustic signal, color-codes the photoacoustic image in preset colors corresponding to the respective damage values of the plurality of regions, and the display displays the color-coded photoacoustic image.

11. The photoacoustic imaging diagnosis apparatus of claim 9, wherein the at least one processor generates a photoacoustic image based on the photoacoustic signal and a time intensity curve (TIC) representing a variation in the intensity of the photoacoustic signal according to time, based on the scan information, and the display displays the TIC and the photoacoustic image.

12. The photoacoustic imaging diagnosis apparatus of claim 11, further comprising an input interface configured to receive an input for setting a region of interest, and
wherein the at least one processor sets the region of interest in the photoacoustic image, based on the input, generates the scan information representing information about the intensity of the photoacoustic signal transmitted from the region of interest, and generates the TIC of the photoacoustic signal transmitted from the region of interest, based on the scan information.

13. The photoacoustic imaging diagnosis apparatus of claim 9, wherein the at least one processor generates a damage value by digitizing the damage degree of the liver, and identifies the excision target region of the liver according to the damage value.

14. The photoacoustic imaging diagnosis apparatus of claim 13, further comprising a storage configured to store excision target regions corresponding to preset values, and
the at least one processor identifies the excision target region corresponding to the damage value by comparing the damage value with the preset values.

15. The photoacoustic imaging diagnosis apparatus of claim 13, wherein the at least one processor generates the scan information comprising information about the intensity of the photoacoustic signal with respect to each of a plurality of regions of the liver, generates a damage value for each of the plurality of regions by digitizing a damage degree in each of the plurality of regions based on the scan information, and determines at least one of the plurality of regions as the excision target region by using the damage value of each of the plurality of regions.

* * * * *